(12) United States Patent  
Li et al.

(10) Patent No.: US 8,535,725 B2  
(45) Date of Patent: Sep. 17, 2013

(54) POROUS-WALL HOLLOW GLASS MICROSPHERES AS CARRIERS FOR BIOMOLECULES

(75) Inventors: Shuyi Li, Martinez, GA (US); William S. Dynan, Martinez, GA (US); George Wicks, Aiken, SC (US); Steven Serkiz, Aiken, SC (US)

(73) Assignees: Georgia Health Sciences University Research Institute, Inc., Augusta, GA (US); Savannah River Nuclear Solutions, LLC, Aiken, SC (US)

( * ) Notice: Subject to any disclaimer, the term of this patent is extended or adjusted under 35 U.S.C. 154(b) by 0 days.

(21) Appl. No.: 13/349,792

(22) Filed: Jan. 13, 2012

(65) Prior Publication Data

US 2012/0201892 A1 Aug. 9, 2012

Related U.S. Application Data

(63) Continuation of application No. PCT/US2010/042117, filed on Jul. 15, 2010.

(60) Provisional application No. 61/271,005, filed on Jul. 16, 2009.

(51) Int. Cl.
*A61K 9/50* (2006.01)
*A61K 51/12* (2006.01)
*A61K 31/721* (2006.01)

(52) U.S. Cl.
CPC . *A61K 9/50* (2013.01); *A61K 9/501* (2013.01); *A61K 51/1286* (2013.01); *A61K 31/721* (2013.01)
USPC .... 424/489; 424/93.6; 424/130.1; 424/135.1; 514/44 R; 514/44 A; 514/7.6

(58) Field of Classification Search
None
See application file for complete search history.

(56) References Cited

U.S. PATENT DOCUMENTS

| | | | |
|---|---|---|---|
| 4,743,545 A * | 5/1988 | Torobin | 435/41 |
| 4,793,980 A | 12/1988 | Torobin | |
| 6,210,715 B1 | 4/2001 | Starling | |
| 7,666,807 B2 | 2/2010 | Heung | |
| 2006/0060820 A1 | 3/2006 | Schumacher | |
| 2007/0037215 A1 | 2/2007 | Patton | |

FOREIGN PATENT DOCUMENTS

| | | |
|---|---|---|
| GB | 2396556 | 6/2004 |
| WO | 2007050362 | 5/2007 |
| WO | 2008069777 | 6/2008 |

OTHER PUBLICATIONS

A Worn, A Pluckthun. "Stability Engineering of Antibody Single-chain Fv Fragments." Journal of Molecular Biology, vol. 305, 2001, pp. 989-1010.*
EG Moss, JM Taylor. "Small-interfering RNAs in the radar of the interferon system." Nature Cell Biology, vol. 5, No. 9, Sep. 2003, pp. 771 and 772.*

(Continued)

*Primary Examiner* — Frederick Krass
*Assistant Examiner* — Isaac Shomer
(74) *Attorney, Agent, or Firm* — Pabst Patent Group LLP

(57) ABSTRACT

The present invention includes compositions of porous-wall hollow glass microspheres and one or more biomolecules, wherein the one or more biomolecules are positioned within a void location within the hollow glass microsphere, and the use of such compositions for the diagnostic and/or therapeutic delivery of biomolecules.

15 Claims, 7 Drawing Sheets

(56) References Cited

OTHER PUBLICATIONS

TC Werner, JR Bunting, RE Cathou. "The Shape of Immunoglobulin G Molecules in Solution." Proceedings of the National Academy of Sciences, vol. 69 No. 4, Apr. 1972, pp. 795-799.*

JA White, WM Deen. "Agarose-Dextran Gels as Synthetic Analogs of Glomerular Basement Membrane: Water Permeability." Biophysical Journal, vol. 82, Apr. 2002, pp. 2081-2089.*

Applied Biosystems, sIRNA design guidelines, Techmical bulletin #506, http://www.ambion.com/techlib/tb/tb_506.html, accessed Jun. 30, 2010.

Chen, et al., "Cotreatment with BCL-2 antagonist sensitizes cutaneous T-cell lymphoma to lethal action of HDAC7-Nur77-based mechanism", Blood; 113:4038-48 (2009).

Franlel, et al., "Antisense oligonucleotide-induced inhibition of adrenocorticotropic hormone release from cultured human corticotrophs", J Neurosurg, 91:261-7 (1999).

Green Car Congress, SRNL develops new permeable miscrospheres; potential for hydrogen storage, http://www.greencarcongress.com/2008/06/srnl-develops-n.html, accessed Jun. 25, 2010.

Heaney and Golde, "Soluble receptors in human disease", J Leukocyte Biology, 64:135-146 (1998).

Juliano, et al., "Mechanisms and strategies for effective delivery of antisense and siRNA oligonucleotides", Nucleic Acids Res; 36:4158-71(2008).

Juliano, "Challenges to macromolecular drug delivery", Biochem Soc Tran,35 (Pt 1):41-3 (2007).

Kim and Rossi, "RNAi mechanisms and applications", Biotechniques; 44:613-6 (2008).

Li, et al., "Modification of the ionizing radiation response in living cells by an scFv against the DNA-dependent protein kinase", Nucleic Acids Res; 31:5848-57 (2003).

Li, "Porous-wall hollow glass microspheres as novel potential nanocarriers for biomedical applications", Nanomedicine, 6(1):127-36 (2010).

Manjunath and Dykxhoorn, "Advances in synthetic siRNA delivery", Discov Med, 9(48):418-30 (2010).

Sato et al., "Unresectable chemorefractory liver metastases: radioembolization with 90Y microspheres—safety, efficacy, and survival", Radiology; 247:507-15 (2008).

Shaki-Loewenstein, et al., "A universal strategy for stable intracellular antibodies", J Immunol Methods; 303:19-39 (2005).

Shi and Huang, "Recent developments of biodegradable and biocompatible materials based micro/nanoparticles for delivering macromolecular therapeutics", Crit Rev Ther Drug Carrier Syst; 26(1):29-84 (2009).

Sibley, et al., "Novel RNA-based strategies for therapeutic gene silencing", Mol Ther; 18(3):466-76 (2010).

Snrl, "Mo-Sci Corporation to manufacture market srnl\s unique glass microsphere", News from the Savannah River National Laboratory (2009).

Taft, et al., "Non-coding RNAs: regulators of disease", J Pathol, 220(2):126-39 (2010).

Tiemann and Rossi, "RNAi-based therapeutics-current status, challenges and prospects", EMBO Mol Med, 1(3):142-51(2009).

Tom and Houle, "Intraspinal microinjection of chondroitinase ABC following injury promotes axonal regeneration out of a peripheral nerve graft bridge", Exp. Neurol, 211(1):315-19 (2008).

Wicks et al., "Microspheres and microworlds", Am Ceram Soc Bull; 87:23-8 (2008).

Witters, et al., "Antisense oligonucleotides to the epidermal growth factor receptor", Breast Cancer Res Treat; 53:41-50 (1999).

Wray, Savannah river researchers unveil permeable, purable glass microballons, post Jun. 8, 2009, http://ceramics.org/about-us/savannah-river-researchers-unveil-permeable-pourable-glass.html., accessed Jun. 15, 2010.

Xiong, et al., "*E. coli* expression of a soluble, active single-chain antibody variable fragment containing a nuclear localization signal", Protein Expr Purif; 66:172-80 (2009).

Yang, et al., "Nanophase ceramics for improved drug delivery", American Ceramic Soc Bull., 89(2):24-32 (2006).

Zhao, et al. "Targeted drug delivery via folate receptors", Expert Opin Drug Deliv; 5:309-19 (2008).

* cited by examiner

A. FITC-dextran (Optical sections)

B. FITC-dextran (Z-stack gallery)

A. DNA
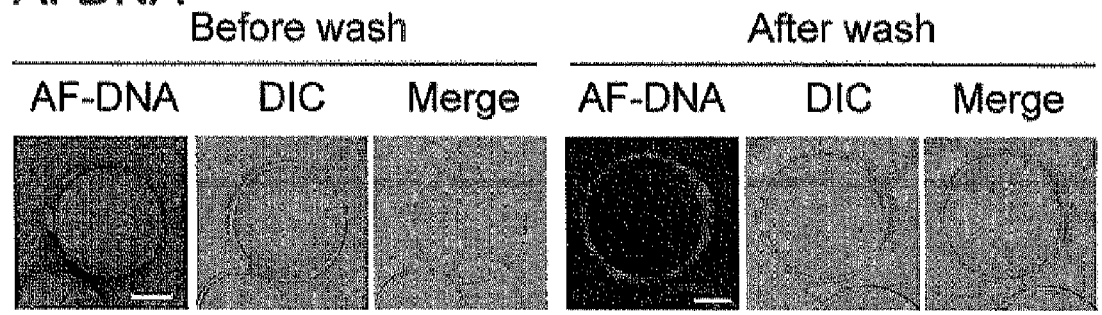
B. RNA
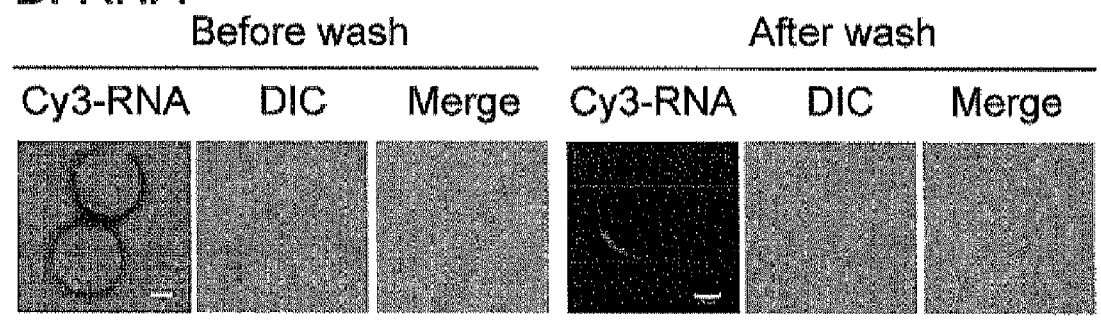
C. RNA with dextran gating
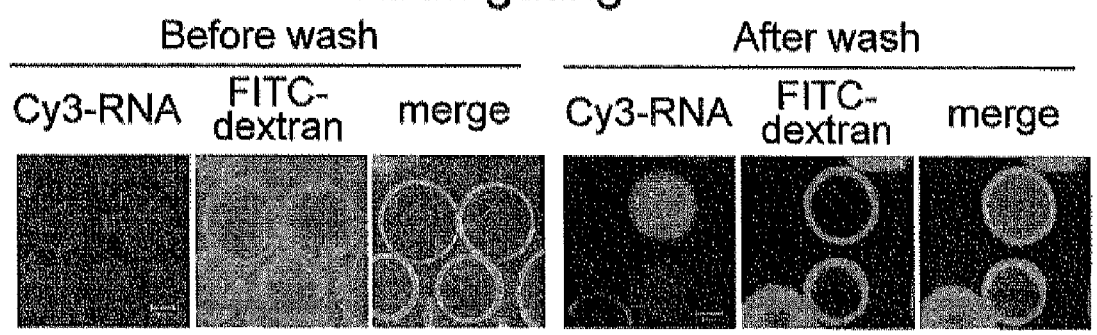
Fig. 5 A-C A. In vitro imaging B. In vivo imaging

SEQUENCE LISTING

```
<160> NUMBER OF SEQ ID NOS: 1

<210> SEQ ID NO 1
<211> LENGTH: 55
<212> TYPE: DNA
<213> ORGANISM: ARTIFICIAL
<220> FEATURE:
<223> OTHER INFORMATION: synthetic oligonucleotide for 5'-Alexa Fluor
      546-labeled probe

<400> SEQUENCE: 1
agcaaaacct catacagaaa attcatttac taacgtctgg aaagacgaca aaact         55
```

POROUS-WALL HOLLOW GLASS MICROSPHERES AS CARRIERS FOR BIOMOLECULES

CROSS REFERENCE TO RELATED APPLICATIONS

This application is a bypass continuation of PCT/US2010/042117 filed under the Patent Cooperation Treaty on Jul. 15, 2010, which claims the benefit of and priority to U.S. Provisional Application Ser. No. 61/271,005, filed on Jul. 16, 2009, the contents of which are incorporated herein by reference in their entirety.

STATEMENT REGARDING FEDERALLY SPONSORED RESEARCH OR DEVELOPMENT

The present invention was made with government support under Grant No. EY018244, awarded by the National Institutes of Health (NIH) Nanomedicine Roadmap Initiative, and Contract No. DE-AC09-08SR22470 awarded by the United States Department of Energy. The Government has certain rights in this invention.

REFERENCE TO SEQUENCE LISTING

The Sequence Listing submitted Jan. 13, 2012, as a text file named "GHSU_2009_026_ST25.txt," created on Jan. 12, 2012, and having a size of 579 bytes is hereby incorporated by reference.

BACKGROUND OF THE INVENTION

Developments in biotechnology have seen the growing use of biomolecules, such as proteins, peptides, vaccines, antibodies, antigens, nucleic acids, and growth factors as therapeutic agents. However, the creation of delivery approaches that combine high specificity for the target cell or tissue, high therapeutic payload, and modest toxicity remains a challenge. See, for example, Juliano, 2007, *Biochem Soc Trans;* 35(Pt 1):41-3 and Shi and Huang, 2009, *Crit. Rev Ther Drug Carrier Syst;* 26(1):29-84. Thus, there is a need for improved drug delivery systems for the delivery of biomolecules. Such improvements will enhance the therapeutic efficacy of such biomolecules and reduce the economic and social burdens of care for previously untreatable or only partially treatable diseases.

SUMMARY OF THE INVENTION

The present invention includes a composition including a hollow glass microsphere having a porous wall surrounding an internal volume and a biopolymer, wherein the biopolymer is positioned within a void location within the hollow glass microsphere.

In some aspects of the compositions of the present invention, the hollow glass microsphere has a diameter ranging from about 10 micron to about 100 microns. In some aspects, the hollow glass microsphere has a diameter ranging from about 20 micron to about 50 microns. In some aspects, the hollow glass microsphere has a diameter of about 8 microns. In some aspects, the hollow glass microsphere has a diameter of about 5 microns.

In some aspects of the compositions of the present invention, the porous wall has a pore diameter of about 1 nanometer (nm) to about 100 nm. In some aspects, the porous wall has a pore diameter of about 10 nanometers (nm).

In some aspects of the compositions of the present invention, the biopolymer is an antibody, or antigen-binding fragment or derivative thereof, a protein, a nucleic acid, a hormone, a growth factor, a virus, or a combination thereof. In some aspects, the biopolymer is a single chain Fv. In some aspects, the biopolymer is a short interfering RNA (siRNA) or an anti-sense RNA.

In some aspects of the compositions of the present invention, the biopolymer has a size about 3 nanometers to about 8 nanometers.

In some aspects of the compositions of the present invention, the porous wall has a pore diameter of a size of about the same size as the biopolymer.

In some aspects of the compositions of the present invention, the porous wall has a pore diameter of a size greater than the size of the biopolymer.

In some aspects of the compositions of the present invention, the composition further includes a gating agent, wherein a gating agent has a size about the same as the size of the pores in the porous wall of the hollow glass microspheres. In some aspects, the gating agent promotes retention of the biopolymer within a void location of the hollow glass microsphere. In some aspects of a composition further including a gating agent, the porous wall has a pore diameter of a size greater than the size of the biopolymer.

In some aspects of the compositions of the present invention, the glass of the hollow glass microsphere is doped with a radioactive isotope.

In some aspects of the compositions of the present invention, a void location comprises the internal volume and/or the porous wall of the hollow glass microsphere.

The present invention includes a composition including a hollow glass microsphere having a porous wall surrounding an internal volume and a gating agent, wherein the gating agent is positioned within a void location within the hollow glass microsphere.

The present invention includes kits including hollow glass microspheres having a porous wall surrounding an internal volume and a gating agent that promotes retention of a biopolymer within a void location of the hollow glass microsphere. In some aspects, a kit may further include one or more biopolymers.

The present invention includes methods of providing a biopolymer to a subject, the method including administering a composition of the present invention to the subject. In some aspects of the method, the composition may be administered intratumorally. In some aspects of the method, the composition may be administered via the hepatic artery. In some aspects of the method, the composition may be delivered as a bone implant. In some aspects of the method, the composition may be delivered topically. In some aspects of the method, the composition may be delivered via a mucosal membrane. In some aspects of the method, the composition may be delivered orally. In some aspects of the method, the composition may be delivered subcutaneously. In some aspects of the method, the composition may be delivered intravenously. In some aspects of the method, the composition may be delivered within one or more joints. In some aspects of the method, the composition may be delivered via the blood supply to a tumor.

The present invention includes systems including a composition of the present invention.

The terms "comprises" and variations thereof do not have a limiting meaning where these terms appear in the description and claims.

Unless otherwise specified, "a," "an," "the," and "at least one" are used interchangeably and mean one or more than one.

BRIEF DESCRIPTION OF THE FIGURES

FIG. 2A is whole microspheres. FIG. 2B is a cross-section of mesoporous wall. Note presence of wormlike ~10-nm-diameter channels.

FIG. 3A is confocal sections showing mixtures of PW-HGMs and fluorescein isothiocyanate (FITC)-labeled dextrans before and after washing with phosphate buffered saline (PBS) to remove free dextran, as indicated. Panels show FITC, differential interference contrast (DIC), and merged images as indicated. Each panel is a single optical slice. Scale bars denote 10 μm. In FIG. 3B, PW-HGMs were incubated with FITC-labeled 70 kDa dextran, then washed with PBS as in FIG. 3A. A series of images is shown representing optical sections along the z-axis for a single PW-HGM.

In FIG. 4A, the indicated FITC-conjugated proteins were incubated individually with PW-HGMs. Molecular weights are provided for each protein (kDa). Confocal images were collected after washing with FBS. Panels show FITC, DIC, and a merged image as indicated. FIG. 4B shows a time course of IgG release. To allow for monitoring over a 20 hour period, images were collected using an Applied Precision Deltavision deconvolution microscope (Applied Precision, Inc., Issaquah, Wash.) with point-visiting capability. Each panel shows a Z-stack projection. In FIG. 4C, MBP-scFv fusion protein was derivatized with folate and FITC and incubated with PW-HGMs, which were washed with fetal bovine serum (FBS). Panels show FITC, bright-field, and deconvolution images. Each panel shows a single optical section. Scale bars denote 10 μm. FIG. 4D shows cell uptake. PW-HGMs were loaded with scFvs, washed with FBS, and allowed to incubate in contact with KB cells for 30 minutes at 37° C. PW-HGMs were removed, and images were collected immediately. Each panel shows a single optical section. Scale bars denote 30 μm.

In FIG. 5A, 5'-Alexa Fluor 546-labeled DNA (AF-DNA; a 55 base pair double-stranded oligonucleotide) was incubated with PW-HGMs. Confocal images were collected before and after washing with PBS. FIG. 5B utilizes the same procedure, but labeling with Cy3-RNA. FIG. 5C is RNA with dextran gating. PW-HGMs were incubated sequentially with Cy3-siRNA and FITC-dextran. Images are shown before and after washing with PBS to remove free RNA and dextran. FIG. 5D is a time course of RNA release, PW-HGMs were incubated sequentially with Cy3-siRNA and FITC-dextran, then washed in PBS and incubated for indicated times before imaging. All panels in this figure represent single optical sections. Scale bars denote 10 μm. DIC, differential interference contrast.

FIG. 6A presents calibration plot showing different amounts of PW-HGM preparation (0-90 μL). PW-HGMs were prepared by incubation with fluorescently labeled 70 kDa dextran and imaged for green fluorescence. Photon counts are represented in arbitrary units. Inset shows gel image and associated false-color intensity bar. FIG. 6B is an image of mouse injected intratumorally with 250 μL of PW-HGM suspension.

DETAILED DESCRIPTION OF ILLUSTRATIVE EMBODIMENTS OF THE INVENTION

The present invention demonstrates for the first time that porous-wall hollow glass microspheres (PW-HGMs) are compatible with biomolecules and are useful as carriers for the delivery of such biomolecules as diagnostic and therapeutic agents. Included in the present invention are compositions of porous-wall hollow glass microspheres and one or more biomolecules and the use of such compositions for the diagnostic and/or therapeutic delivery of biomolecules.

Figure 1:
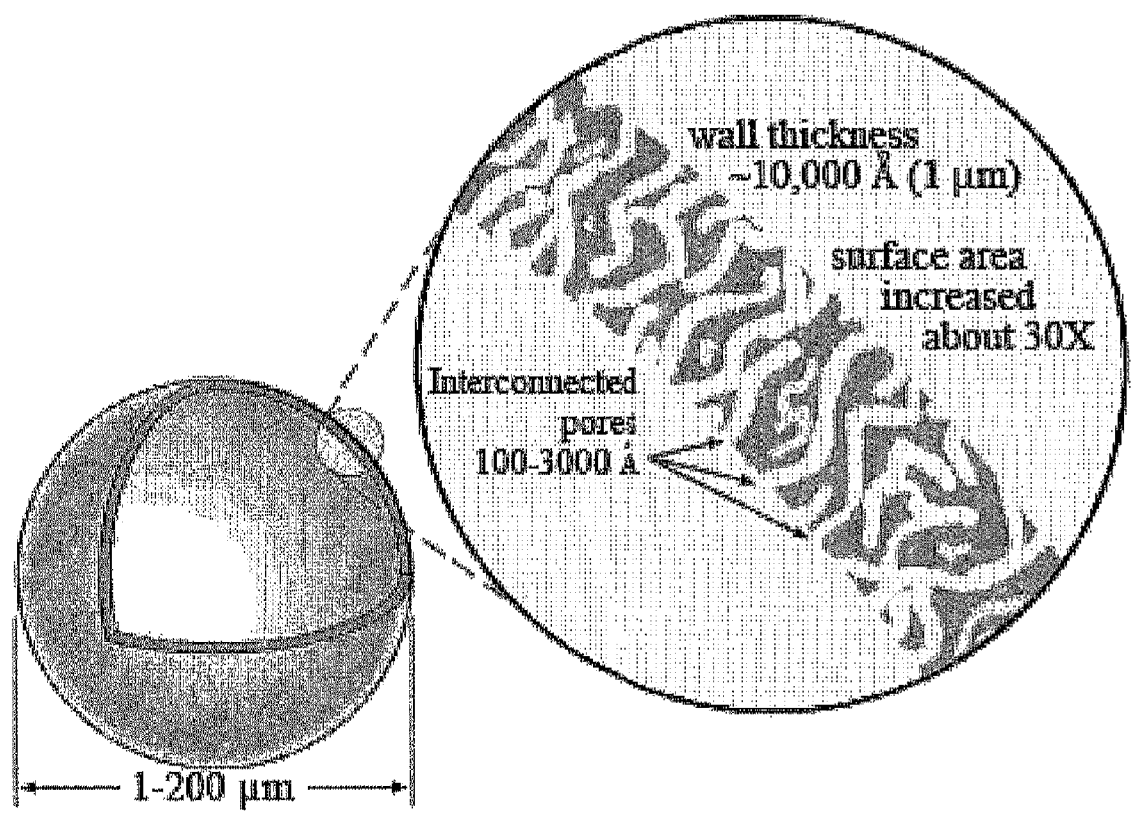
FIG. 1. Schematic representations of a porous-wall hollow glass microspheres (PW-HGMs) and wall porosity (Wicks et al., 2008, *Am Ceram Soc Bull;* 87:23-8).

Porous-wall hollow glass microspheres are a novel form of glass material having a hollow central cavity surrounded by a silica shell. This shell may have a thickness of about 1 micrometer (μm) to about 2 μm. The wall of the silica shell is mesoporous, with a tortuous network of nanometer-scale channels, also referred to herein as pores, penetrating the shell and connecting the outside with the interior central cavity. See FIG. 1, FIG. 2A and FIG. 2B. This combination of a hollow central cavity that can carry therapeutic agents with mesoporous walls for controlled release is a unique characteristic that distinguishes PW-HGMs from other glass materials currently available for biomedical applications.

Porous-wall hollow glass microspheres, also referred to herein as porous wall hollow glass microspheres, hollow porous-wall glass microspheres, hollow porous wall glass microspheres, PW-HGMs, PW-HGM, PWHGMs, PWHGM HP-WGMs HP-WGMs, HPWGMs, HPWGM, may be produced by any of a variety of methods, including, but not limited to, those described in more detail in WO 2008/069777; WO 2007/050362; U.S. Pat. No. 7,666,807; U.S. patent application Ser. No. 10/946,464, filed Sep. 21, 2004; U.S. patent application Ser. No. 12/315,544, and Wicks et al., 2008, *Am Ceram Soc Bull;* 87:23-8, each of which is incorporated by reference herein. For example, porous-wall hollow glass microspheres may be produced following, but not limited to, procedures as described in Example 1.

Porous-wall hollow glass microspheres for use in the compositions of the present invention include porous-wall hollow glass microspheres with any of a variety of diameters. For example, porous-wall hollow glass microspheres used in the compositions of the present invention may have a diameter range of sizing of about 1 micron to about 200 microns, about 1 micron to about 180 microns, about 1 micron to about 140 microns, about 1 micron to about 100 microns, about 1 micron to about 80 microns, about 1 micron to about 50 microns, about 1 micron to about 10 microns, about 2 microns to about 200 microns, about 2 microns to about 180 microns, about 2 microns to about 140 microns, about 2 microns to about 100 microns, about 2 microns to about 80 microns, about 2 microns to about 50 microns, about 2 microns to about 20 microns, about 2 microns to about 10 microns, about 5 microns to about 200 microns, about 5 microns to about 180 microns, about 5 microns to about 140 microns, about 5 microns to about 100 microns, about 5 microns to about 80 microns, about 5 microns to about 50 microns, about 5 microns to about 20 microns, about 5 microns to about 10 microns, about 10 microns to about 200 microns, about 10 microns to about 180 microns, about 10 microns to about 140 microns, about 10 microns to about 100 microns, about 10 microns to about 80 microns, about 10 microns to about 50 microns, about 10 microns to about 20 microns, about 20 microns to about 200 microns, about 20 microns to about 180 microns, about 20 microns to about 140 microns, about 20 microns to about 100 microns, about 20 microns to about 80 microns, about 20 to about 50 microns, about 50 microns to about 200 microns, about 50 microns to about 180 microns, about 50 microns to about 140 microns, about 50 microns to about 100 microns, or about 50 microns to about 80 microns. A micron may also be referred to herein as a micrometer or μm.

In some embodiments, porous-wall hollow glass microspheres may have a diameter range of sizing of about 10 microns to about 100 microns. In some embodiments, porous-wall hollow glass microspheres may have a diameter range of sizing of about 20 microns to about 50 microns.

Porous-wall hollow glass microspheres used in the compositions of the present invention may have a diameter of about 200 microns or less, about 180 microns or less, about 140 microns or less, of about 100 microns or less, of about 80 microns or less, of about 50 microns or less, of about 20 microns or less, of about 10 microns or less, or of about 8 microns or less.

Preparations of porous-wall hollow glass microspheres used in the compositions of the present invention may have an average diameter of about 200 microns, about 180 microns, about 140 microns, about 100 microns, about 80 microns, about 50 microns, about 20 microns, about 10 microns, about 8 microns, or about 5 microns.

In some embodiments, a preparation of porous-wall hollow glass microspheres for use in the compositions of the present invention may be monodisperse, that is, may be a preparation of porous-wall hollow glass microspheres of a uniform size. For example, a preparation of porous-wall hollow glass microspheres may be greater than about 50% in the specified size range, greater than about 75% in the specified size range, greater than about 90% in the specified size range, or greater than about 95% in the specified size range.

In some embodiments, a preparation of porous-wall hollow glass microspheres for use in the compositions of the present invention may be greater than about 50% true spheres, greater than about 75% true spheres, greater than about 90% true spheres, or greater than about 95% true spheres.

In some embodiments, porous-wall hollow glass microspheres may have a diameter sizing to allow unhindered movement through the vascular system, that is, having a diameter similar to or less than that of an erythrocyte (7 to 8 μm) or a leukocyte (7 to 18 μm) and able to move through a capillary bed. For example, such porous-wall hollow glass microspheres may have a diameter of less than about 10 microns, of about 8 microns or less, or of about 8 microns, of about 5 microns or less, or of about 5 microns.

In some embodiments, porous-wall hollow glass microspheres have a diameter sizing that hinders movement through the vascular system, that is, having a diameter greater than that of an erythrocyte (7 to 8 μm) or a leukocyte (7 to 18 μm) and not able to move through a capillary bed. Such porous-wall hollow glass microspheres may lodge within a capillary bed, the veins and/or the arteries. For example, porous-wall hollow glass microspheres may have a diameter of greater than about 10 microns or of about 20 microns to about 50 microns. Compositions of such porous-wall hollow glass microspheres may be used in applications wherein the inability to pass through the microvasculature is either not required or is an advantage, for example, in methods of tumor embolization.

Porous-wall hollow glass microspheres exhibit a high degree of wall porosity. As used herein, the term "porosity" means a series of pores and similar openings which either directly or indirectly define a series of passageways which provide communication between the interior and the exterior of the hollow glass microsphere. Porous-wall hollow glass microspheres of the present invention may have any of a range of porosities. For example, wall porosity (also referred to herein as pore size) may be about 1 nanometer (nm) to about 300 nanometers, about 1 nanometer to about 100 nanometers, about 10 nanometers to about 300 nanometers, about 10 nanometers to about 100 nanometers, or about 1 nanometers to about 10 nanometers. With the present invention wall porosity may be about 1 nanometer, about 10 nanometers, about 20 nanometers, about 50 nanometers, about 75 nanometers, about 100 nanometers, or about 300 nanometers. With the present invention wall porosity may be about 1 nanometer or more, about 10 nanometers or more, about 20 nanometers or more, about 50 nanometers or more, about 75 nanometers or more, or about 100 nanometers or more. With the present invention wall porosity may be about 1 nanometer or less, about 10 nanometers or less, about 20 nanometers or less, about 50 nanometers or less, about 75 nanometers or less, about 100 nanometers or less, or about 300 nanometers or less. Nanometers may also be referred to herein as Angstroms, wherein an Angstrom is 0.1 nanometer. Any of these measurements may reflect an average measurement of pore size. Porosity may be modified, for example, by altering or reducing the overall pore size or by coating the individual porous-wall hollow glass microspheres.

Porous-wall hollow glass microspheres of the present invention may have a density of, for example, about 0.05 gram per cubic centimeter (gm/cc) to about to about 2.0 gm/cc, of about 0.05 gm/cc to about 0.5 gm/cc, and of about 1.0 gm/cc to about 2.0 gm/cc. Porous-wall hollow glass microspheres may be separated on the basis of density so as to select and segregate the hollow glass microspheres according to desired densities.

Porous-wall hollow glass microspheres for use in the compositions of the present invention may be made of medical grade glass and may be produced under quality control procedures that comply with good manufacturing practices and EU and FDA requirements. The composition of the glass, flame temperature, residence time, and cooling rate may all be adjusted to produce PW-HGMs that are best suited for biomedical applications.

In some embodiments, the glass itself of porous-wall hollow glass microspheres may include one or more further ingredients dissolved, diffused, or suspended within the glass. Such doping materials may include, but are not limited to, colorants, radioisotopes, fluorescent dyes, magnetic iron oxides, rare earth ions, MRI contrast agents, such as, for example, iron or manganese, and other detectable agents. The glass of porous-wall hollow glass microspheres may be doped with one or more radioisotopes, such as, for example, $^{90}Y$, and may be used in methods of therapeutic radiation delivery. Solid glass spheres doped with $^{90}Y$ have shown promise for the treatment of liver cancer (see, for example, Sato et al., 2008, *Radiology;* 247:507-15).

With the present invention, void locations within porous-wall hollow glass microspheres are filled with one or more biomolecules, including, but not limited to biopolymers and/or other biologically active macromolecules. Void locations include the hollow central cavity of the microspheres, also referred to herein as an internal volume, and/or the porous openings of the mesoporous walls of the microspheres. Such compositions of porous-wall hollow glass microspheres filled with one or more biomolecules may be used in a variety of therapeutic and diagnostic methods. Compositions of the present invention may also be multifunctional, for use for both diagnostic imaging and therapeutic purposes. The biocompatibility and long-term safety of glass materials have led to widespread medical use. However, glass materials currently used in biomedical applications are solid. The presence of a hollow interior cavity carrying one or more soluble therapeutic biomolecules and the ability to control release via the porous walls are unique characteristics that make the compositions of the present invention, porous-wall hollow glass microspheres filled with one or more biomolecules, unlike any previous compositions of glass materials for biomedical applications.

Compositions of the present invention include one or more biomolecules, including, but not limited to, biopolymers and other biologically active macromolecules. Such a biomolecule, biopolymer, or biologically active macromolecule may be an isolated biomolecule, isolated biopolymer, or isolated biologically active macromolecule. As used herein, "isolated" refers to material that has been either removed from its natural environment (e.g., the natural environment if it is naturally occurring), produced using recombinant techniques, or chemically or enzymatically synthesized, and thus is altered "by the hand of man" from its natural state.

As used herein, a biomolecule is a molecule found in a biological system. In some aspects, a biomolecule is not an element or inorganic compound, for example, is not hydrogen or a metal. As used herein, a biopolymer is a polymer of one or more types of repeating units. Biopolymers are found in biological systems and include, but are not limited to, polypeptides and polynucleotides. Biopolymers often have a well defined structure. The exact chemical composition and the sequence in which these units are arranged is called the primary structure. Biopolymers may spontaneously fold into characteristic compact shapes (also referred to as secondary structure and tertiary structure), which help determine their biological functions.

A biopolymer may have a size that is about the same size as the pore diameter size within the porous wall of the hollow glass microspheres. A biopolymer may have a size that is less that the pore diameter size within the porous wall of the hollow glass microspheres. In some embodiments, a biopolymer may have a size of about 3 nanometers to about 8 nanometers.

A biopolymer may be polynucleotide. Specifically, a polynucleotide biopolymer includes DNA (including cDNA), RNA and oligonucleotides, regardless of the source. An oligonucleotide generally refers to a nucleotide multimer of about 10 to 100 nucleotides in length, while a polynucleotide includes a nucleotide multimer having any number of nucleotides. This includes polynucleotides in which the conventional backbone has been replaced with a non-naturally occurring or synthetic backbone, and nucleic acids in which one or more of the conventional bases has been replaced with a synthetic base capable of participating in Watson-Crick type hydrogen bonding interactions.

As used herein, the term "nucleotide" refers to a ribonucleotide or a deoxyribonucleotide or modified form thereof, as well as an analog thereof. Nucleotides include species that comprise purines, e.g., adenine, hypoxanthine, guanine, and their derivatives and analogs, as well as pyrimidines, e.g., cytosine, uracil, thymine, and their derivatives and analogs. Nucleotide analogs include nucleotides having modifications in the chemical structure of the base, sugar and/or phosphate, including, but not limited to, 5-position pyrimidine modifications, 8-position purine modifications, modifications at cytosine exocyclic amines, and substitution of 5-bromouracil; and T-position sugar modifications, including but not limited to, sugar-modified ribonucleotides in which the 2'-OH is replaced by a group such as an H, OR, R, halo, SH, SR, NH2, NHR, NR2, or CN, wherein R is an alkyl moiety. Nucleotide analogs are also meant to include nucleotides with bases such as inosine, queuosine, xanthine, sugars such as 2'-methyl ribose, non-natural phosphodiester linkages such as methylphosphonates, phosphorothioates and peptides. Modified bases refer to nucleotide bases such as, for example, adenine, guanine, cytosine, thymine, uracil, xanthine, inosine, and queuosine that have been modified by the replacement or addition of one or more atoms or groups. Some examples of types of modifications that can comprise nucleotides that are modified with respect to the base moieties include but are not limited to, alkylated, halogenated, thiolated, aminated, amidated, or acetylated bases, individually or in combination. More specific examples include, for example, 5-propynyluridine, 5-propynylcytidine, 6-methyladenine, 6-methylguanine, N,N,-dimethyladenine, 2-propyladenine, 2-propylguanine, 2-aminoadenine, 1-methylinosine, 3-methyluridine, 5-methylcytidine, 5-methyluridine and other nucleotides having a modification at the 5 position, 5-(2-amino)propyl uridine, 5-halocytidine, 5-halouridine, 4-acetylcytidine, 1-methyladenosine, 2-methyladenosine, 3-methylcytidine, 6-methyluridine, 2-methylguanosine, 7-methylguanosine, 2,2-dimethylguanosine, 5-methylaminoethyluridine, 5-methyloxyuridine, deazanucleotides such as 7-deaza-adenosine, 6-azouridine, 6-azocytidine, 6-azothymidine, 5-methyl-2-thiouridine, other thio bases such as 2-thiouridine and 4-thiouridine and 2-thiocytidine, dihydrouridine, pseudouridine, queuosine, archaeosine, naphthyl and substituted naphthyl groups, any O- and N-alkylated purines and pyrimidines such as N6-methyladenosine, 5-methylcarbonylmethyluridine, uridine 5-oxyacetic acid, pyridine-4-one, pyridine-2-one, phenyl and modified phenyl groups such as aminophenol or 2,4,6-trimethoxy benzene, modified cytosines that act as G-clamp nucleotides, 8-substituted adenines and guanines, 5-substituted uracils and thymines, azapyrimidines, carboxyhydroxyalkyl nucleotides, carboxyalkylaminoalkyl nucleotides, and alkylcarbonylalkylated nucleotides. Modified nucleotides also include those nucleotides that are modified with respect to the sugar moiety, as well as nucleotides having sugars or analogs thereof that are not ribosyl. For example, the sugar moieties may be, or be based on, mannoses, arabinoses, glucopyranoses, galactopyranoses, 4'-thioribose, and other sugars, heterocycles, or carbocycles.

A polynucleotide may be single-stranded or double-stranded. In some aspects, a polynucleotide biopolymer may be complementary to a given sequence. As used herein, the term "complementary" refers to the ability of polynucleotides to form base pairs with one another. Base pairs are typically formed by hydrogen bonds between nucleotide units in anti-parallel polynucleotide strands. Complementary polynucleotide strands can base pair in the Watson-Crick manner (e.g., A to T, A to U, C to G), or in any other manner that allows for the formation of duplexes. As persons skilled in the art are aware, when using RNA as opposed to DNA, uracil rather than thymine is the base that is considered to be complementary to adenosine. However, when a U is denoted in the context of the present invention, the ability to substitute a T is implied, unless otherwise stated.

A polynucleotide biopolymer may be a small interfering RNA (siRNA) or an antisense RNA or DNA. Antisense nucleic acids are DNA or RNA molecules that are complementary to at least a portion of a specific mRNA molecule. Such antisense nucleic may be about 15 to about 35 bases in length. For example, 20-mer oligonucleotides have been shown to inhibit the expression of the epidermal growth factor receptor mRNA (Witters et al., 1999, *Breast Cancer Res*

Treat; 53:41-50) and 25-mer oligonucleotides have been shown to decrease the expression of adrenocorticotropic hormone by greater than 90% (Franlel et al., 1999, *J Neurosurg*; 91:261-7). However, it is appreciated that it may be desirable to use oligonucleotides with lengths outside this range, for example 10, 11, 12, 13, or 14 bases or 36, 37, 38, 39, or 40 bases. Oligonucleotides with lengths of about 40 bases, about 45 bases, about 50 bases, about 55 bases, about 60 bases, about 65 bases, about 70 bases, about 75 bases or longer may also be desirable. Any of a variety of methods are available for preparing antisense DNA or RNA, such as for example, chemical synthesis, in vitro transcription, expression vectors, and PCR expression cassettes.

It has been recently shown that when short RNA duplexes are introduced into mammalian cells, sequence-specific inhibition of target mRNA can be realized without inducing an interferon response. Certain of these short dsRNAs, referred to as small inhibitory RNAs (siRNAs), can act catalytically at sub-molar concentrations to cleave greater than 95% of the target mRNA in the cell. These molecules contain varying degrees of complementarity to their target mRNA in the antisense strand. A siRNA may vary in length and may be for example, about 15 to about 35 bases, about 19 to about 23 bases, about 21 bases. Some, but not all, siRNA have unpaired overhanging bases on the 5' or 3' end of the sense strand and/or the antisense strand. The term "siRNA" includes duplexes of two separate strands, as well as single strands that can form hairpin structures comprising a duplex region. Methods of preparing siRNAs are known to those skilled in the art and preclinical studies and early clinical trials are demonstrating the utility of small interfering RNAs (siRNAs) for the treatment of cancer, viral infections, as well as a wide range of additional diseases. For reviews, see, for example, Manjunath and Dykxhoorn, 2010, *Discov Med*; 9(48):418-30; Sibley et al., 2010, *Mol Ther*; 18(3):466-76; Tiemann and Rossi, 2009, *EMBO Mol Med*; 1(3):142-51; and Taft et al., 2010, *J Pathol*; 220(2):126-39. In addition to siRNA, a nucleic acid biopolymer may be a repeat associated small interfering RNA (rasiRNA), a Piwi-interacting RNA (piRNA), or microRNA (miRNA). A variety of methods are available for preparing such RNAs, such as for example, chemical synthesis, in vitro transcription, RNA expression vectors, and PCR expression cassettes. Guidelines for designing a siRNA and choosing the siRNA target site are known to the skilled artisan. For example, see, Applied Biosystem's Technical Bulletin #506 ("siRNA Design Guidelines;" available on the worldwide web at ambion.com/techlib/tb/tb_506.html).

A polynucleotide biopolymer may include a polynucleotide for gene therapy applications. Such a polynucleotide may encode a therapeutically effective polypeptide. A polynucleotide biopolymer may include a vector, such as for example, a viral vector or a plasmid vector.

A biopolymer may be a polypeptide. The polypeptide may be any polypeptide having a biological activity of interest. The term "polypeptide" is not meant herein to refer to a specific length of the encoded product and, therefore, encompasses peptides, oligopeptides, and proteins. The term "polypeptide" may also encompass two or more polypeptides combined to form the encoded product. Polypeptides also include hybrid polypeptides, which comprise a combination of partial or complete polypeptide sequences obtained from at least two different polypeptides.

A polypeptide biopolymer may be, for example, an antibody, antigen, antimicrobial peptide, enzyme, growth factor, hormone, cytokine, neurotransmitter, receptor, reporter protein, structural protein, or transcription factor. As used herein, a growth factor is a polypeptide that, at least, promotes cell growth of induces phenotypic changes. Examples of growth factors include, but are not limited to, bone morphological proteins (such as, for example, Bone Morphological Protein 1 (BMP1), Bone Morphological Protein 2 (BMP2), Bone Morphological Protein 3 (BMP3), Bone Morphological Protein 4 (BMP4), Bone Morphological Protein 5 (BMP5), Bone Morphological Protein 6 (BMP6), or Bone Morphological Protein 7 (BMP7)), Epidermal Growth Factor (EGF), Erythropoietin (EPO), Fibroblast Growth Factor (FGF), Granulocyte-colony stimulating factor (G-CSF), Granulocyte-macrophage colony stimulating factor (GM-CSF), Growth differentiation factor-9 (GDF9), Hepatocyte growth factor (HGF), Hepatoma derived growth factor (HDGF), Insulin-like growth factors (such as, for example Insulin-Like Growth Factor-1 (IGF-1) and Insulin-Like Growth Factor-2 (IGF-2)), Keratinocyte Growth Factor (KGF), Myostatin (GDF-8), Nerve growth factor (NGF) and other neurotrophins, placental growth factor (PlGF), Platelet-derived growth factor (PDGF), Thrombopoietin (TPO), Transforming growth factor alpha (TGF-a), Transforming growth factor beta (TGF-β), Vascular endothelial growth factor (VEGF), Interleukin-1 (IL-1), Interleukin-2 (IL-2), Interleukin-3 (IL-3), Interleukin-4 (IL-4), Interleukin-5 (IL-5), Interleukin-6 (IL-6), Interleukin-7 (IL-7), Interleukin-8 (IL-8), Tumor Necrosis Factor-α (TNF-α), Tumor Necrosis Factor-β (TNF-β), Interferon-γ (INF-β) and Colony Stimulating Factor (CSF).

A polypeptide biopolymer may be a cytokine, interleukin or chemotactic cytokine. Cytokines are secreted primarily from leukocytes and may stimulate humoral and/or cellular immune responses, as well as the activation of phagocytic cells. Cytokines that are secreted from lymphocytes are termed lymphokines, whereas those secreted by monocytes or macrophages are termed monokines. Examples, include, for example, Interleukin-1α (IL-1α), Interleukin-1β (IL-1β), Interleukin-2 (IL-2), Interleukin-3 (IL-3), Interleukin-4 (IL-4), Interleukin-5 (IL-5), Interleukin-6 (IL-6), Interleukin-7 (IL-7), Interleukin-8 (IL-8), Interleukin-9 (IL-9), Interleukin-10 (IL-10), Interleukin-11 (IL-11), Interleukin-12 (IL-12), Interleukin-13 (IL-13), Interleukin-14 (IL-14), Interleukin-15 (IL-15), Interleukin-16 (IL-16), Interleukin-17 (IL-17), Interleukin-18 (IL-18), Interferon-α (INF-α), Interferon-β (INF-β), and Interferon-γ (INF-γ). Growth factors, cytokines, interleukins, and chemokines may be purified from an appropriate tissue or cell source, chemically or recombinantly produced, or obtained from a commercial source.

A polypeptide biopolymer may be a soluble receptor polypeptide, including, but not limited to, tumor necrosis factor (TNF) receptor, IL-1 receptor, IL-2 receptor, IL-4 receptor, IL-6 receptor, IL-7 receptor, IL-11 receptor, I-12 receptor, intercellular adhesion molecule-1 (ICAM-1/CD54), stem cell factor receptor (c-kit), interferon receptor, Fas (CD95), nerve growth factor receptor, CD27, CD30, growth hormone receptor, GM-CSF receptor, erythropoietin receptor, thrombopoietin receptor, G-CSF receptor, lipopolysaccharide receptor (CD14), complement receptor Type I (CD35), hyaluronate receptor (CD44), CD58, IgE receptor (FceRII, CD23), IgG receptor (FcgRII), ICAM-3 (CD50), transforming growth factor receptor, epidermal growth factor receptor (c-erb B), vascular endothelial growth factor receptor, platelet derived growth factor receptor, fibroblast growth factor receptor, colony stimulating factor-1 receptor, insulin receptor, and insulin-like growth factor-II receptor.

A polypeptide biopolymer may be an enzyme, or fragment thereof. Such a fragment may be enzymatically active. A polypeptide polymer may also include polyethylene glycol conjugates of an enzyme or fragment thereof. A polypeptide polymer may include any of a wide variety of therapeutic enzymes, including, but not limited to, adenosine deaminase ((used, for example, as a therapeutic agent for the treatment of adenosine deaminase (ADA) deficiency), asparaginase ((used, for example, as a therapeutic agent for the treatment of acute lymphoblastic leukemia (ALL)), catalase, glucocerebrosidase, alpha-L-iduronidase (used, for example, as a therapeutic agent for the treatment of mucopolysaccharidosis type I (Hurler syndrome)), chondroitin sulfate proteoglycans (CSPG)-digesting enzyme chondroitinase ABC (ChABC), phenylalanine ammonia-lyase (used, for example, as a therapeutic agent for the treatment of phenylketonuria (PKU)), superoxide dismutase (SOD), digestive enzymes, and pancreatic enzymes.

A polypeptide biopolymer may be an antibody. As used herein, an antibody includes substantially intact antibody molecules, as well as chimeric antibodies, humanized antibodies, human antibodies, single chain antibodies, bispecific antibodies, multispecific antibodies, anti-idiotypic antibodies, antibody heavy chains, antibody light chains, intracellularly-made antibodies (i.e., intrabodies), homodimers and heterodimers of antibody heavy and/or light chains, single-chain Fvs (scFv), disulfide-linked Fvs (sdFV), Fab fragments, F(ab') fragments, F(ab')2 fragments, Fv fragments, diabodies, linear antibodies fragments produced by a Fab expression library, fragments comprising either a VL or VH domain and antigen binding fragments and derivatives of the same.

An antibody may be a polyclonal antibody or a monoclonal antibody. A monoclonal antibody composition displays a single binding specificity and affinity for a particular epitope. Antibodies may be produced in animals and cells, including mammalian and plant cells, produced recombinantly, or chemically synthesized. An antibody may be of any type (e.g., IgG, IgE, IgM, IgD, IgA and IgY), class (e.g., IgG1, IgG2, IgG3, IgG4, IgA1 and IgA2) or subclass of immunoglobulin molecule. Immunoglobulins can have both heavy and light chains. An array of IgG, IgE, IgM, IgD, IgA, and IgY heavy chains can be paired with a light chain of the kappa or lambda form.

A human antibody includes antibodies having variable regions in which both the framework and CDR regions are derived from human germline immunoglobulin sequences. Furthermore, if the antibody contains a constant region, the constant region also is derived from human germline immunoglobulin sequences. In some aspects, an antibody may be from a species other than human, for example, mouse, rat, hamster, rabbit, chicken, turkey, camel, or illama.

Humanised antibodies include antibodies in which complementary determining regions of a human antibody (recipient antibody) are replaced by residues from a complementary determining region of a non human species (donor antibody) such as, for example, mouse, rat, rabbit, hamster, chicken, turkey, camel, or Mama, having the desired functionality.

The antigen-binding function of an antibody can be performed by fragments of a full-length antibody and a biopolymer may be an antigen-binding portion of an antibody. The term "antigen-binding" portion or fragment of an antibody, as used herein, refers to that portion of an antibody molecule, within the variable region, that is required to bind the antigen of interest. The antigen-binding portion contains the amino acid residues that interact with an antigen and confer on the antibody its specificity and affinity for the antigen. Like an intact antibody, an antigen binding fragment retains the ability to specifically bind to an antigen. As used herein, "specific binding" refers to antibody binding to a predetermined antigen. Typically, the antibody binds with a dissociation constant ($K_D$) of $10^{-8}$ M or less, and binds to the predetermined antigen with a $K_D$ that is at least two-fold less than its $K_D$ for binding to a non-specific antigen (such as, for example, BSA) other than the predetermined antigen or a closely-related antigen.

Antigen binding fragments can be obtained using methods well known in the art. For example, antibody fragments according to the present invention can be prepared by proteolytic hydrolysis of the antibody or by expression in E. coli or mammalian cells (including Chinese hamster ovary cell culture and other protein expression systems) of DNA encoding the fragment. Alternatively, antibody fragments can be obtained by pepsin or papain digestion of whole antibodies by conventional methods. The advantages of using antibody fragments, rather than whole antibodies, are several-fold. The smaller size of the fragments may lead to improved pharmacological properties, such as better penetration of solid tissue. Moreover, antigen-binding fragments such as Fab, Fv, ScFv and dAb antibody fragments can be expressed in and secreted from E. coli, thus allowing the facile production of large amounts of the said fragments.

Examples of antigen binding fragments of an antibody include, for example, Fab fragment (a monovalent fragment consisting of the VL, VH, CL and CH1 domains), Fab' fragments, F(ab')2 fragment (a bivalent fragment comprising two Fab fragments linked by a disulfide bridge at the hinge region), Fd fragment (the VH and CH1 domains), Fv fragment (the VL and VH domains of a single arm of an antibody), single-chain Fvs (scFv), disulfide-linked Fvs (sdFv), diabodies, domain Ab fragments (including single (dAbs) and dual formats (dAb-linker-dAb), single domain antibody (sdAb, called nanobodies, a single monomeric variable antibody domain).

One advantage of antibody binding fragments is the smaller size of the fragments. Intact antibodies, composed of two heavy chains and two light chains, have a molecular weight of about 150 to 160 kilodaltons (kDa) while, for example, Fab fragments (composed of one light chain and half a heavy chain) have a molecular weight of about 50 kDa, scFv (composed of two variable domains, one from a light and one from a heavy chain) have a molecular weight of about 25 kDA, and sdAbs have a molecular weight of about 12 to 15 kDa.

Included with the present invention are antibodies and antigen binding fragments that are further engineered and/or modified to engineer a modified antibody, which modified antibody may have altered properties from the starting antibody. For example, an antibody can be engineered by modifying one or more residues within one or both variable regions, for example within one or more CDR regions and/or within one or more framework regions. Additionally or alternatively, an antibody can be engineered by modifying residues within the constant region(s), for example to alter the effector function(s) of the antibody. In addition or alternative to modifications made within the framework or CDR regions, antibodies of the invention may be engineered to include modifications within the Fc region, typically to alter one or more functional properties of the antibody, such as serum half-life, complement fixation, Fc receptor binding, and/or antigen-dependent cellular cytotoxicity. Furthermore, an antibody may be chemically modified. For example, one or more chemical moieties can be attached to the antibody or its glycosylation may be modified, again to alter one or more functional properties of the antibody.

Any of a variety of therapeutic or diagnostic antibodies are included with the present invention. For example, antibodies for use in the compositions and methods of the present invention may include Abciximab (a chimeric antibody for inhibition of glycoprotein IIb/IIIa in the treatment of cardiovascular disease), Adalimumab ((Humira), a human antibody, for inhibition of TNF-α signaling in the treatment of autoimmune disordersm such as rheumatoid arthritis), Alemtuzumab ((Mabcampath), a humanized antibody to CD52 for treatment of chronic lymphocytic leukemia), Arcitumomab, Basiliximab (a chimeric IL-2Ra receptor antibody for use in prevention of transplant rejection), Bevacizumab ((Avastin), humanized antibody to vascular endothelial growth factor (VEGF) for use in treatment of colorectal cancer), Capromab, Cetuximab ((Erbitux), a chimeric antibody to epidermal growth factor receptor for treatment of colorectal cancer and head and neck cancer), Certolizumab (a humanized antibody for inhibition of TNF-a signaling for treatment of Crohn's disease), Cotara, Daclizumab (a humanized antibody to the IL-2Ra receptor (CD25), for treatment of transplant rejection), Eculizumab ((Soliris), a humanized antibody to complement system protein C5 for the treatment of paroxysmal nocturnal hemoglobinuria), Edrecolomab, Efalizumab ((Raptiva), a humanized antibody to CD11a for the treatment of psoriasis), Fanolesomab/Technetium99m (Neutrospec), Gemtuzumab ((Mylotarg), a humanized antibody to CD33 for the treatment of acute myelogenous leukemia), Ibritumomab tiuxetan, ((Zevalin), a murine antibody to CD20 for the treatment of Non-Hodgkin lymphoma (with yttrium-90 or indium-111)), Igovomab, Infliximab ((Remicade), a chimeric antibody for the inhibition of TNF-a signaling in the treatment of autoimmune disorders), Muromonab-CD3 ((Orthoclone OKT3), a murine antibody to T cell CD3 Receptor for the treatment of transplant rejection), Natalizumab ((Tysabri), a humanized antibody to alpha-4 integrin for the treatment of multiple sclerosis and Crohn's disease), Nofetumomab, Omalizurnab ((Xolair), a humanized antibody to immunoglobulin E (IgE) for the treatment of mainly allergy-related asthma), Palivizumab ((Synagis) a humanized antibody to an epitope of the RSV F protein for the treatment of Respiratory Syncytial Virus), Panitumumab ((Vectibix), a human antibody to epidermal growth factor receptor for the treatment of colorectal cancer), Ranibizumab ((Lucentis), a humanized antibody to vascular endothelial growth factor A (VEGF-A) for the treatment of macular degeneration), Rituximab ((Rituxan), a chimeric antibody to CD20 for the treatment of various cancers, such as Non-Hodgkin lymphoma), Satumomab, Sulesomab, Tositumomab ((Bexxar), a murine antibody to CD20 for the treatment of Non-Hodgkin lymphoma), Trastuzumab ((Herceptin), a humanized antibody to ErbB2 for use in the treatment of breast cancer), and Votumumab.

Antibodies for use in the compositions and methods of the present invention include antibodies with a specificity for a protein important in radiation repair mechanisms. For example, such an antibody may be specific for DNA-dependent protein kinase, an enzyme important in non-homologous end joining (NHEJ), a pathway that repairs DNA damage caused by ionizing radiation. Examples include monoclonal antibody 18-2, antigen binding fragments thereof; such as, for example, scFv 18-2, and modifications thereof, such as, for example, a maltose-binding protein (MBP) fusion to scFv 18-2 (Li et al., 2003, *Nucleic Acid Res;* 31(20):5848-5857).

A biopolymer may be a polysaccharide or other carbohydrate polymer. The polysaccharide may be, for example, a mucopolysaccharide, such as, for example, heparin and hyaluronic acid, and nitrogen-containing polysaccharide, such as, for example, chitin. Compositions of the present invention may include other biologically active macromolecules, such as, for example, viruses and viral particles and complexes or conjugates of biopolymers.

Importantly, with the present invention, it has been shown that the porous channels of porous-wall hollow glass microspheres promote size-dependent uptake and controlled release of biomolecules. Further, it has been shown that gating agents within the composition can facilitate the controlled release of a biomolecule internalized within porous-wall hollow glass microspheres. Thus, compositions of the present invention may further include one or more gating agents. As used herein, a gating agent is a soluble, pharmacolgically inert molecule. A gating agent may have a molecular size that is about the same size as, or slightly smaller than, the pore diameter size within the porous wall of the hollow glass microspheres. In some embodiments, a gating agent may have a molecular size of about 3 nanometers to about 8 nanometers, or about 6 nanometers. A gating agent may be used to gate the porous walls of a glass microsphere, facilitating the retention and controlled release of an internalized biomolecule that has a molecular size that is smaller than the pore diameter size of the hollow glass microspheres. Examples of gating agents include, for example, dextran, colloidal starch, hydroxyethyl starch, gelatin, oxypolygelatin, albumin, plasma protein fraction, colloids, and water soluble synthetic polymers, such as, for example, polyvinylpyrrolidone. In some embodiments, dextran with a molecular of about 10 to about 150 kilodaltons may be used. In some embodiments, dextran with a molecular of about 10 kilodaltons, about 20 kilodaltons, about 40 kilodaltons, about 60 kilodaltons, about 70 kilodaltons, or about 150 kilodaltons may be used.

Biopolymers and other biologically active macromolecules may be modified to include additional components, including, for example, carbohydrates, lipids, detectable label, such as, for example, such as for example a radioactive or fluorescent moiety, or a mass label, magnetic nanoparticles, and agents to increase biological half life, such as, for example, of polyethylene glycol or other suitable polymer. Such components may be covalently attached.

A further embodiment of the present invention includes compositions of porous-wall hollow glass microspheres filled with one or more agents that are not biologically active macromolecules, including biopolymers, for use in a variety of therapeutic and diagnostic methods, including, but not limited to, any of those described herein. Thus, such compositions do not include a biologically active macromolecule, including a biopolymer. Such compositions may be multifunctional, for use in both diagnostic imaging and therapeutic purposes. Such compositions may further include one or more gating agents. Such agents may include, but are not limited to, antibiotics and other antibacterial agents, antiviral agents, antifungal agents, anthelmintics, anti-inflammatory agents, such as, for example, salicylic acid, indomethacin, NSAIDS, and COX-2 inhibitors, analgesics, corticosteroids, anticancer drugs, antiemetics, cardiovascular agents, antiarrhythmic agents, antihypertensive agents, anticoagulants, insulin, antiepileptics, antihistamines, antimycobacterial agents, antineoplastic agents, immunosuppressants, sedatives, beta-adrenoceptor blocking agents, contrast media, diagnostic agents, diagnostic imaging agents, diuretics, dopaminergics, haemostatics, immunological agents, lipid regulating agents, muscle relaxants, prostaglandins, radiopharmaceuticals, vasodilators, an organ-transplant rejection therapy, a drug, a mineral or nutrient, a dye, a vitamin, an adjuvant, colorants, radioisotopes, fluorescent dyes, magnetic iron oxides, rare earth ions, MRI contrast agents, and other detectable agents.

The compositions of the present invention include a mixture or cocktail of two, three, four, five, or more biopolymers. In addition to one or more biomolecules, compositions of the present invention may include one or more additional therapeutic agents. Such an additional agent is not a biopolymer. Such agents may include, but are not limited to, antibiotics and other antibacterial agents, antiviral agents, antifungal agents, anthelmintics, anti-inflammatory agents, such as, for example, salicylic acid, indomethacin, NSAIDS, and COX-2 inhibitors, analgesics, corticosteroids, anticancer drugs, antiemetics, cardiovascular agents, antiarrhythmic agents, antihypertensive agents, anticoagulants, insulin, antiepileptics, antihistamines, antimycobacterial agents, antineoplastic agents, immunosuppressants, sedatives, beta-adrenoceptor blocking agents, contrast media, diagnostic agents, diagnostic imaging agents, diuretics, dopaminergics, haemostatics, immunological agents, lipid regulating agents, muscle relaxants, prostaglandins, radio-pharmaceuticals, vasodilators, an organ-transplant rejection therapy, a drug, a mineral or nutrient, a dye, a vitamin, or an adjuvant.

Compositions of the present invention may include one or more accessory ingredients including, but not limited to, diluents, buffers, binders, disintegrants, surface active agents, thickeners, lubricants, preservatives (including antioxidants), solvents, diluents, preservatives to retard microbial or fungal growth, absorption delaying agents, carrier solutions, suspensions, colloids, and the like. The preparation and use of such compositions is well known in the art. A composition may be a pharmaceutically acceptable composition, meaning that the composition is not biologically or otherwise undesirable, and the material may be administered to a subject without causing any undesirable biological effects or interacting in a deleterious manner with any of the other components of the pharmaceutical composition in which it is contained. The compositions of the present invention are formulated in pharmaceutical preparations in a variety of forms adapted to the chosen route of administration. For parenteral administration a composition may be an aqueous solution, for example, the solution may be suitably buffered to maintain the pH in an acceptable range and the composition may be rendered isotonic with sufficient saline or glucose. These particular aqueous solutions are especially suitable for intravenous, intramuscular, subcutaneous, intraperitoneal, and intratumoral administration. For human administration, preparations should meet sterility, pyrogenicity, and general safety and purity standards as required by the FDA. Such preparation may be pyrogen-free.

The compositions of the present invention may be administered to an individual in need thereof by any of a wide variety of means. For example, a composition may be delivered topically (including transdermal, aerosol, buccal and sublingual), transmucosally, orally, rectally, vaginally, parenterally (including subcutaneous, intramuscular, intravenous and intradermal), intranasally, intrathecally, intracranially, and/or intraarticularly. Delivery may be by local delivery or injection. Delivery may include injection into or around the tumor. Delivery may be by embolization, including, but not limited to tumor embolization and the embolization of other tissues and organs. A composition of the present invention may provide controlled release over a prolonged period of time. A composition of the present invention may serve as an implant. Compositions of the present invention may enhance endocytosis of drugs by target cells and may also facilitate deeper penetration into capillaries and through fenestrations to, ultimately, enhanced cellular uptake. The use of compositions of the present invention for the delivery of biomolecules and other agents presents several advantages, including, reduce toxicity, prevention of immunogenic or antigenic side reactions, prevention of random distribution of drugs throughout a patient's body, facilitating targeting of an agent to a tissue or organ, reduced dosing frequency, improved patient adherence, minimized fluctuation of drug concentrations and maintenance of blood levels within a desired range, localized drug delivery, and the potential for reduced adverse effects and increased safety.

The compositions of the present invention may be used in a wide variety of treatment and/or diagnostic methods. As used herein "treating" or "treatment" may include therapeutic and/or prophylactic treatments. Desirable effects of treatment include preventing occurrence or recurrence of disease, alleviation of symptoms, diminishment of any direct or indirect pathological consequences of the disease, decreasing the rate of disease progression, amelioration or palliation of the disease state, and remission or improved prognosis. "Diagnosis" refers to diagnosis, prognosis, monitoring, characterizing, selecting patients, including participants in clinical trials, and identifying patients at risk for or having a particular disorder or clinical event or those most likely to respond to a particular therapeutic treatment, or for assessing or monitoring a patient's response to a particular therapeutic treatment.

Therapeutically effective concentrations and amounts may be determined for each application herein empirically by testing the compounds in known in vitro and in vivo systems, such as those described herein, dosages for humans or other animals may then be extrapolated therefrom.

It is understood that the precise dosage and duration of treatment is a function of the disease being treated and may be determined empirically using known testing protocols or by extrapolation from in vivo or in vitro test data. It is to be noted that concentrations and dosage values may also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed compositions and methods.

An agent of the present invention may be administered at once, or may be divided into a number of smaller doses to be administered at intervals of time. It is understood that the precise dosage and duration of treatment is a function of the disease being treated and may be determined empirically using known testing protocols or by extrapolation from in vivo or in vitro test data. It is to be noted that concentrations and dosage values may also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed compositions and methods.

With the methods of the present invention, the efficacy of the administration of one or more agents may be assessed by any of a variety of parameters well known in the art. In some therapeutic embodiments, an "effective amount" of an agent is an amount that results in a reduction of at least one pathological parameter. Thus, for example, in some aspects of the present invention, an effective amount is an amount that is effective to achieve a reduction of at least about 10%, at least about 15%, at least about 20%, or at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, or at least about 95%, compared to the expected reduction in the parameter in an individual not treated with the agent.

The compositions of the present invention may also be administered to a patient for the treatment of cancer. In some aspects, the composition may be administered in a manner that results in tumor embolization. Cancers to be treated by the present invention include, but are not limited to, melanoma, basal cell carcinoma, colorectal cancer, pancreatic cancer, breast cancer, prostate cancer, lung cancer (including small-cell lung carcinoma and non-small-cell carcinoma, leukemia, lymphoma, sarcoma, liver cancer, ovarian cancer, Kaposi's sarcoma, Hodgkin's Disease, Non-Hodgkin's Lymphoma, multiple myeloma, neuroblastoma, rhabdomyosarcoma, primary thrombocytosis, primary macroglobulinemia, primary brain tumors, stomach cancer, malignant pancreatic insulanoma, malignant carcinoid, urinary bladder cancer, premalignant skin lesions, testicular cancer, lymphomas, thyroid cancer, neuroblastoma, esophageal cancer, genitourinary tract cancer, malignant hypercalcemia, cervical cancer, endometrial cancer, glioblastoma, medulloblastomas, and adrenal cortical cancer. The efficacy of treatment of a cancer may be assessed by any of various parameters well known in the art. This includes, but is not limited to, determinations of a reduction in tumor size, determinations of the inhibition of the growth, spread, invasiveness, vascularization, angiogenesis, and/or metastasis of a tumor, determinations of the inhibition of the growth, spread, invasiveness and/or vascularization of any metastatic lesions, determinations of tumor infiltrations by immune system cells, and/or determinations of an increased delayed type hypersensitivity reaction to tumor antigen. The efficacy of treatment may also be assessed by the determination of a delay in relapse or a delay in tumor progression in the subject or by a determination of survival rate of the subject, for example, an increased survival rate at one or five years post treatment. As used herein, a relapse is the return of a tumor or neoplasm after its apparent cessation.

Biomolecules to be delivered for the treatment of cancer include, but are not limited to, polypeptides, siRNAs, and antibodies. In some aspects, the administration of a composition to a patient for the treatment of cancer may be further supplemented with the administration of one or more additional anti-cancer agents. Such agents may be included in the compositions. Such agents may be included in the internal void volume of the glass microspheres. In some aspects, an additional anti-cancer agent is radiation therapy. Such radiation may be delivered by an external source or may be included within the glass the microspheres.

The compositions of the present invention may be administered to a patient to facilitate bone healing. Biomolecules to be delivered include, but are not limited to, bone morphogenetic proteins, such as, for example BMP2 or BMP7. Compositions may include additional agents, such as, for example, small molecule drugs, antibiotics, minerals, vitamins, and/or gating agents. Such compositions may be used in the treatment, for example, of bone fracture, bone nonunion, skull bone formation, bone tumors, and tooth formation. Such compositions may be delivered, for example, as an implant into bone tissue.

The compositions of the present invention may be administered to a patient to facilitate wound healing. For example, biomolecules to be delivered include, but are not limited to, growth factors that promote healing, such as for example, epidermal growth factor, vascular endothelial growth factor, fibroblast growth factor, and keratinocyte growth factor. Compositions may include additional agents, such as, for example, small molecule drugs, antibiotics, minerals, vitamins, and/or gating agents. Such compositions may be used in the treatment of, for example, pressure ulcers, venous ulcers, diabetic ulcers, decubitus ulcer, and non-healing surgical incisions. Such compositions may be delivered, for example, topically to a wound site.

The compositions of the present invention may be administered to a patient in methods to modulate immune responses, including enhancing or suppressing an immune response. For example, the compositions may include any of a variety of cytokines to control inflammation.

The compositions of the present invention are useful for the topical delivery of biomolecules to various body cavities, for example in the treatment of laryngeal, nasopharyngeal, and oropharyngeal cancers. The compositions of the present invention are useful for localized delivery of biomolecules to tumors, wound sites, and other pathogenic sites. Such compositions may be delivered, for example, topically, orally, subcutaneously, intravenously, by injection or implantation directly into a tissue location, or delivered in a manner that results in embolization.

The compositions of the present invention are useful as a controlled-release vehicle for medications, including, for example, the delivery of insulin in diabetes therapy or the delivery of erythropoietin in the treatment of anemia. Compositions of the present invention may function as an implant. Such compositions may be delivered, for example, topically, orally, subcutaneously, intravenously, by injection or implantation directly into a tissue location, or delivered in a manner that results in embolization.

The compositions of the present invention may also be administered directly into a joint for the treatment of, for example, cancer, gout, osteoarthritis, bursitis, psoriatic arthritis, tendinitis, hemarthrosis, and rheumatoid arthritis. Biomolecules to be delivered include, but are not limited to, antibodies, such as anti-TNFα antibodies, siRNA, and polypeptides. Compositions may include additional agents, such as, for example, small molecule drugs, antibiotics, minerals, vitamins, radioisotopes, anti-inflammatory agents, steroids, and/or gating agents.

The compositions of the present invention are useful for the delivery of antiviral agents, including, for example, siRNA, for the treatment of a variety of conditions, including, but not limited to, cervical precancerous lesions, dermatological conditions, and ophthalmic diseases.

The compositions of the present invention are useful for the delivery of antibacterial agents to a variety of locations, including, but not limited to, the outer or middle ear, surgical incisions, and wound sites, and useful in the treatment of infections.

As used herein, the term "subject" includes, but is not limited to, humans and non-human vertebrates. In preferred embodiments, a subject is a mammal, particularly a human. A subject may be an individual. A subject may be a patient. Non-human vertebrates include livestock animals, companion animals, and laboratory animals. Non-human subjects also include non-human primates as well as rodents, such as, but not limited to, a rat or a mouse. Non-human subjects also include, without limitation, chickens, horses, cows, pigs, goats, dogs, cats, guinea pigs, hamsters, mink, and rabbits.

The methods of the present invention include in vivo and in vitro methods. As used herein "in vitro" is in cell culture and "in vivo" is within the body of a subject.

The compositions of the present invention may be presented, for example, as a kit, in a pack, or as a dispenser device. Such presentations may contain one or more unit dosage forms containing one or more active ingredients. The kit or pack may for example, comprise metal or plastic foil, such as a blister pack. The kit, pack, or dispenser device may be accompanied by instructions for preparation and/or administration. The active agents may be packaged as articles of manufacture containing packaging material, an agent provided herein, and a label that indicates the disorder for which the agent is provided. A kit of the present invention may include, for example, as one component, hollow glass microspheres having a porous wall surrounding an internal volume and, as a second component, a gating agent that promotes retention of a biopolymer within a void location of the hollow glass microsphere. Such a kit may or may not include, as additional further components, one or more biopolymers.

The present invention includes methods of detecting a cancer or other pathogenic condition. In some aspects, the detection may be presymptomatic. Such detection methods may include the transformation of matter. For example, the status of the sample after the detection step is altered from the status of the sample, as originally provided.

The therapeutic and detection methods of the present invention may include providing a report summarizing the results. Such a report may be provided, for example, in written or electronic formats.

The methods of the present invention and/or one or more portions thereof may be implemented in hardware or software, or a combination of both. For example, the functions described herein may be designed in conformance with the principles set forth herein and implemented as one or more integrated circuits using a suitable processing technology, e.g., CMOS. As another example, the present invention may be implemented using one or more computer programs executing on programmable computers, such as computers that include, for example, processing capabilities, data storage (e.g., volatile and nonvolatile memory and/or storage elements), input devices, and output devices. Program code and/or logic described herein is applied to input data to perform functionality described herein and generate desired output information. The output information may be applied as an input to one or more other devices and/or processes, in a known fashion. Any program used to implement the present invention may be provided in a high level procedural and/or object orientated programming language to communicate with a computer system. Further, programs may be implemented in assembly or machine language. In any case, the language may be a compiled or interpreted language. Any such computer programs may preferably be stored on a storage media or device (e.g., ROM or magnetic disk) readable by a general or special purpose program, computer, or a processor apparatus for configuring and operating the computer when the storage media or device is read by the computer to perform the procedures described herein. The system may also be considered to be implemented as a computer readable storage medium, configured with a computer program, where the storage medium so configured causes the computer to operate in a specific and predefined manner to perform functions described herein.

The present invention and/or one or more portions thereof may include circuitry that may include a computer system operable to execute software to provide for the determination of a physiological state. Although the circuitry may be implemented using software executable using a computer apparatus, other specialized hardware may also provide the functionality required to provide a user with information as to the physiological state of the individual. As such, the term circuitry as used herein includes specialized hardware in addition to or as an alternative to circuitry such as processors capable of executing various software processes. The computer system may be, for example, any fixed or mobile computer system, e.g., a personal computer or a minicomputer. The exact configuration of the computer system is not limiting and most any device capable of providing suitable computing capabilities may be used according to the present invention. Further, various peripheral devices, such as a computer display, a mouse, a keyboard, memory, a printer, etc., are contemplated to be used in combination with a processing apparatus in the computer system. In view of the above, it will be readily apparent that the functionality as described herein may be implemented in any manner as would be known to one skilled in the art.

The present invention is illustrated by the following examples. It is to be understood that the particular examples, materials, amounts, and procedures are to be interpreted broadly in accordance with the scope and spirit of the invention as set forth herein.

EXAMPLES

Example 1

Porous-Wall Hollow Glass Microspheres as Novel Potential Nanocarriers for Biomedical Applications Porous-wall hollow glass microspheres (PW-HGMs) are a novel form of glass material consisting of a 10- to 100-μm-diameter hollow central cavity surrounded by a 1-μm-thick silica shell. A tortuous network of nanometer-scale channels completely penetrates the shell. This example demonstrates that these channels promote size-dependent uptake and controlled release of biological molecules in the 3- to 8-nm range, including antibodies and a modified single-chain antibody variable fragment. In addition, a 6 nm (70 kDa) dextran was used to gate the porous walls, facilitating controlled release of an internalized short interfering RNA. PW-HGMs remained in place after mouse intratumoral injection, suggesting a possible application for the delivery of anticancer drugs. The combination of a hollow central cavity that can carry soluble therapeutic agents with mesoporous walls for controlled release is a unique characteristic that distinguishes PW-HGMs from other glass materials for biomedical applications. The channels of PW-HGMs allow size-dependent uptake and controlled release of biological molecules including antibodies and single-chain antibody fragments. PW-HGMs remained in place after mouse intratumoral injection, supporting application for the delivery of anti-cancer drugs.

The present example demonstrates that PW-HGMs are useful as nanocarriers for controlled delivery of macromolecular therapeutics. This example tested their ability to interact with proteins, carbohydrates, and nucleic acids and found that small dextrans, proteins, and nucleic acids (less than ~3 nm diameter) pass freely in and out of the interior cavity of the PW-HGMs in a rapid and reversible interaction, whereas some larger molecules (5-6 nm diameter) enter the interior cavity but also adhere strongly to the channel walls. One of these, a 70 kDa dextran, can be used to gate the channels, allowing retention and slow release of a short interfering RNA (siRNA). The results indicate that PW-HGMs will be useful as a controlled-release delivery vehicle for antibodies or recombinant antibody derivatives, as well as small oligonucleotides.

Methods

Fabrication of porous-wall hollow glass microspheres. The process and apparatus for producing PW-HGMs has been described, along with methodologies for loading or filling these materials. See, for example, WO 2007/050362; WO 2008/069777; U.S. Pat. No. 7,666,807; Published U.S. Patent Application 2006-0060820; and U.S. patent application Ser. No. 12/315,544, each of which is incorporated herein in its entirety.

Briefly, feed for producing PW-HGMs was a 20- to 40-μm sodium borosilicate glass powder, and containing a sulfate blowing agent. The powder was fed into a hot zone produced by a controlled gas-air flame, which softens the glass to allow formation of spherical particles. The blowing agent becomes unstable as it is heated, producing a glass bubble that expands to produce hollow glass microspheres. The material was quenched, and a flotation process was used to retrieve the desired initial products. These were heat-treated to produce two phases in the thin outer walls, one rich in silica and the other in sodium and boron. The hollow microspheres were treated with 4 M HCl, which preferentially leaches the sodium- and boron-rich phase, leaving interconnected channels in the silica-rich phase. In some experiments (as noted in the legends to figures), dry sieving was performed to enrich for <20 μm-diameter PW-HGMs. Scanning electron microscopy (SEM) and other physical analyses were conducted at the Savannah River National Laboratory and at the Electron Microscopy Facility at Clemson University.

Fluorescently labeled dextrans, proteins, and nucleic acids. Fluorescein-labeled dextrans were obtained from Sigma-Aldrich (St. Louis, Mo.). Fluorescently labeled DNA was prepared by annealing a 5'-Alexa Fluor 546-labeled oligonucleotide d(AGCAAAACCTCATACAGAAAATTCATTTACTA ACGTCTGGAAAGACGACAAAACT) (SEQ ID NO:1), from Invitrogen (Carlsbad, Calif.) to its unlabeled complement. Cy3-labeled glyceraldehyde-3-phosphate dehydrogenase siRNA was from Applied Biosystems (Austin, Tex.). Alexa Fluor 488-labeled goat anti-rabbit IgG was obtained from Invitrogen. Other proteins were from High Molecular Weight and Low Molecular Weight Gel Filtration Calibration Kits (GE Healthcare Life Sciences, Buckinghamshire, UK). A maltose-binding protein (MBP) fusion to single-chain antibody variable fragment (scFv) 18-2 (Li et al., 2003, Nucleic Acids Res; 31:5848-57) was expressed in *Escherichia coli*, purified as described by Xiong et al., 2009, Protein Expr Purif; 66:172-80), and reacted with Traut's reagent and folate-N-succimydyl 3-(2-pyridyldithio)-propionate (Thermo Scientific/Pierce, Rockford, Ill.). For protein labeling, a 100 μg/mL solution of fluorescein isothiocyanate (FITC; Sigma-Aldrich, St. Louis, Mo.) was prepared in dimethylsulfoxide. A separate solution of each protein was prepared in phosphate-buffered saline (PBS), adjusted to pH 7.5-8.0 with sodium carbonate. FITC was added at a 3:1 molar ratio and reacted at 37° C. for 30 minutes, and the labeled product was separated by gel filtration chromatography using Sephadex G-25 (Pre-packed Disposable Columns PD-10, Cat. no. 17-0851-01; GE Healthcare Life Sciences).

Dextran, protein, and nucleic acid loading. Dry PW-HGMs (2-3 mg) were suspended in 50-100 μL of PBS containing 200 μg/mL of dextran, 200 μg/mL protein, or 2 μM nucleic acid and incubated at room temperature (20-25° C.) for 5-10 minutes. An aliquot was transferred to a glass-bottom microwell dish (MatTek Corp., Ashland, Mass.) for direct observation. The remainder was collected by gentle centrifugation, washed with 0.5 mL of phosphate buffered saline (PBS) or fetal bovine serum (FBS), and centrifuged again to remove excess dextran, nucleic acid, or protein. The pellet was resuspended in 50-100 μL of PBS or FBS for imaging. For sequential incubation experiments, 2 μM DNA or siRNA was incubated with PWHGMs for 5-10 minutes, FITC-dextran (70 kDa, 200 μg/mL) was added, and incubation was continued for another 5-10 minutes. Washing was performed as described. Microscopy was performed using a Zeiss LSM 510 laser scanning confocal microscope (Carl Zeiss Microlmaging, Inc. Thornwood, N.Y.) with a 40× or a 63× oil objective or an Applied Precision Deltavision microscope (Applied Precision, Inc., Issaquah, Wash.) with a 20× or a 60× oil objective.

Figure 6:
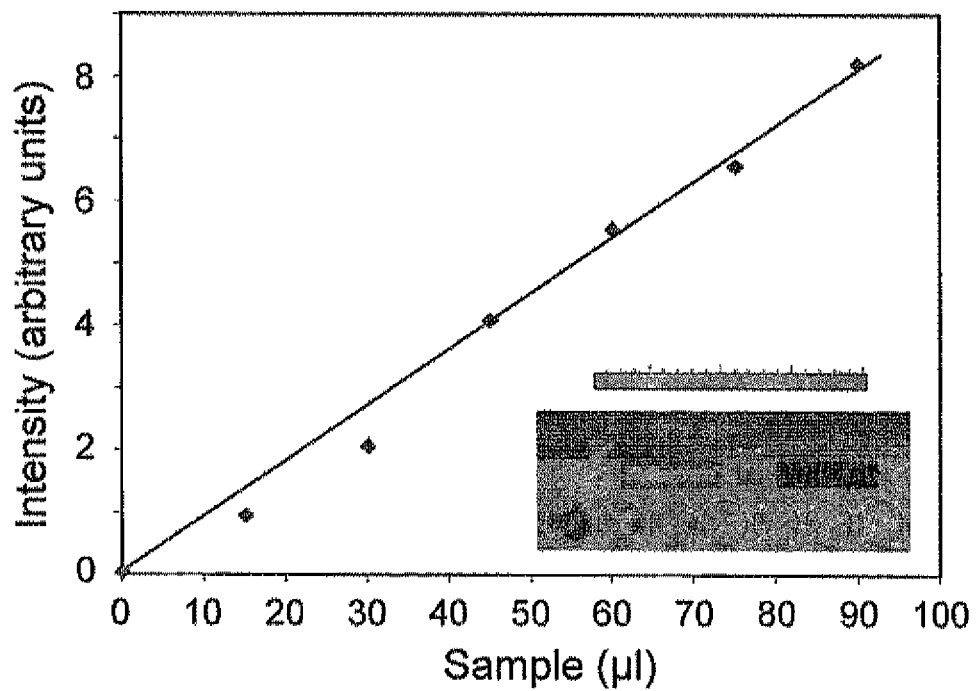
FIG. 6. Retention of FITC-dextran-labeled PW-HGMs in a mouse tumor.
Figure 6:
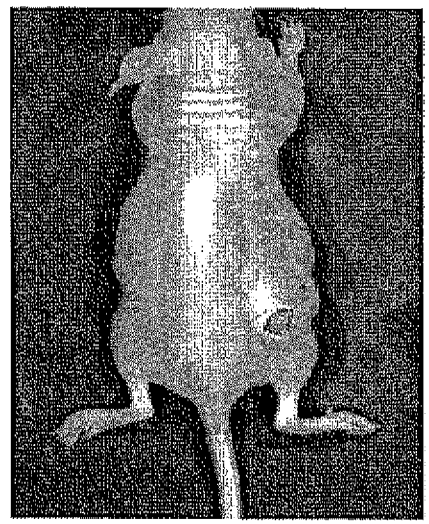

Intratumoral injection. PW-HGMs (3.3 mg) were incubated with fluorescein-labeled 70-kDa dextran (200 μg/mL) in 100 μL PBS. Just before use, PW-HGMs were washed twice with PBS and resuspended in 500 μL of PBS. To quantify signal from a known amount of PW-HGMs, aliquots were withdrawn from the center of a uniform suspension using a cut-off 200 μL pipette tip, and the volumes indicated in the description to FIG. 6 were transferred to the wells of a 1% (wt/vol) agarose gel. PBS was added to each well to bring the final volume to 100 μL. Animal experiments were performed at the Medical College of Georgia according to an Institutional Animal Care and Use Committee-approved protocol. To prepare for PW-HGM injection, 10$^7$ cells of the HH human cutaneous T-cell lymphoma line were injected into the flank of a 6- to 8-week-old nude mouse (Harlan Labs, Inc., San Diego, Calif.) which was held until the tumor reached a volume of 200-300 mm3 (Chen et al., 2009, *Blood;* 113: 4038-48). A 250 μl, volume of prepared PW-HGMs was withdrawn from suspension using a 22 gauge needle syringe and injected intratumorally at a depth of approximately 5 mm. Care was taken to avoid any excess PW-HGMs on the surface of the tumor, and the procedure was validated by the brightfield images of the animals. The mouse was anesthetized with a 1:1 mixture of medical air and oxygen containing 2% isoflurane and maintained at this level on a heated stage during the subsequent imaging session. Fluorescence images were collected using a Xenogen IVIS Imaging System (Caliper Life Sciences, Hopkinton, Mass.) equipped with a 445 to 490 nm bandpass filter for excitation and a 515 to 575 nm bandpass filter for emissions. Images were acquired with a 1-second exposure, and Living-Image 2.60 Software (Caliper Life Sciences, Hopkinton, Mass.) was used to perform a fluorescent overlay, which allowed the subtraction of background to produce the final images.

Results

Figure 2:
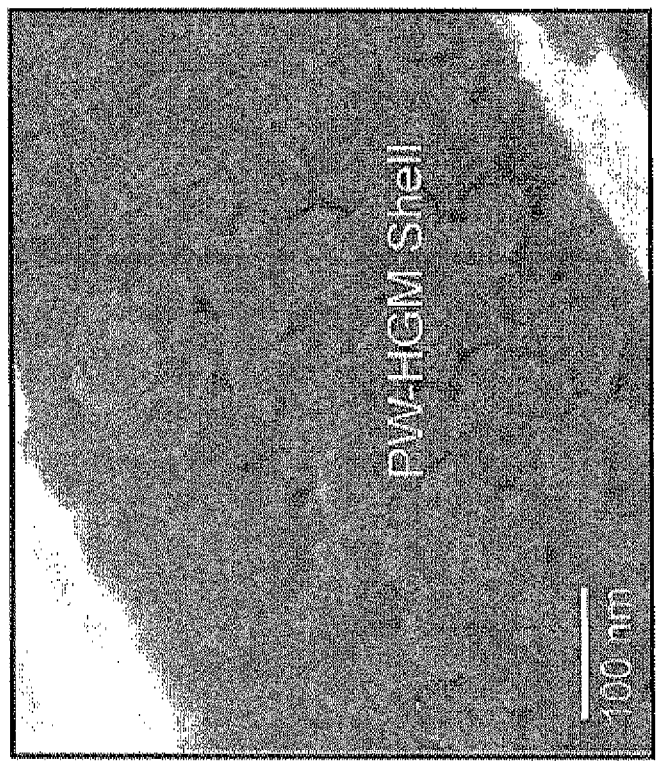
FIG. 2. Structure of porous-wall hollow glass microspheres (PW-HGMs). Typical scanning electron micrographs of PW-HGMs.
Figure 2:
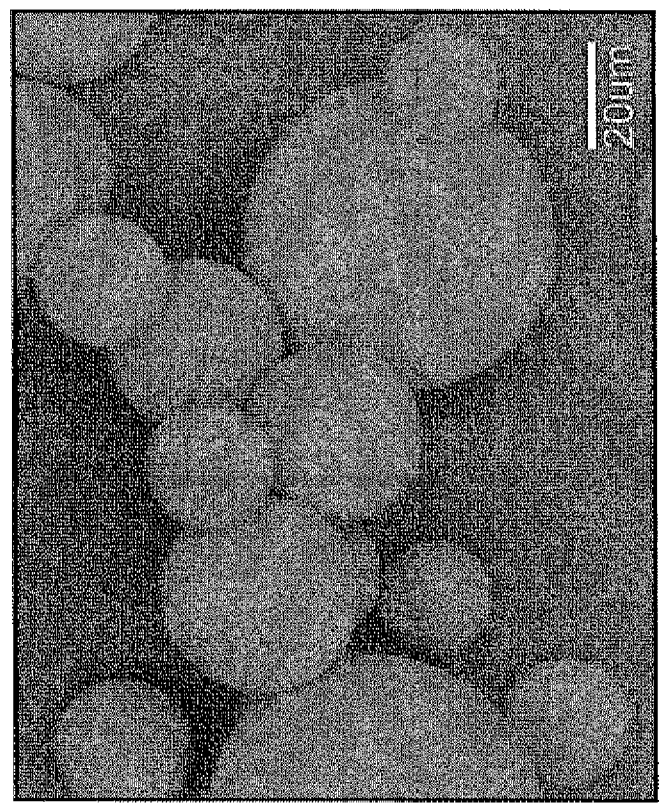

Characterization of porous wall hollow glass microspheres. Representative batches of PW-HGMs were characterized by pycnometer densitometry, mercury intrusion porosimetry, optical microscopy, and SEM. The densities of PW-HGMs were 1.5-2.0 g/mL, and diameters ranged from 10 to 100 μm, with a mean of about 50 μm. The ink bottle-shaped pores had diameters ranging from about 10 nm, at the narrowest point, to about 300 nm. A SEM image of the PW-HGMs shows the smooth outer surface (FIG. 2A). A higher magnification view shows the typical wall thickness of 1 μm and reveals the porosity in the outer shell (FIG. 2B). These pores, which connect the exterior space with the interior volume of the microspheres, are the distinguishing characteristic of PW-HGMs.

Figure 3:
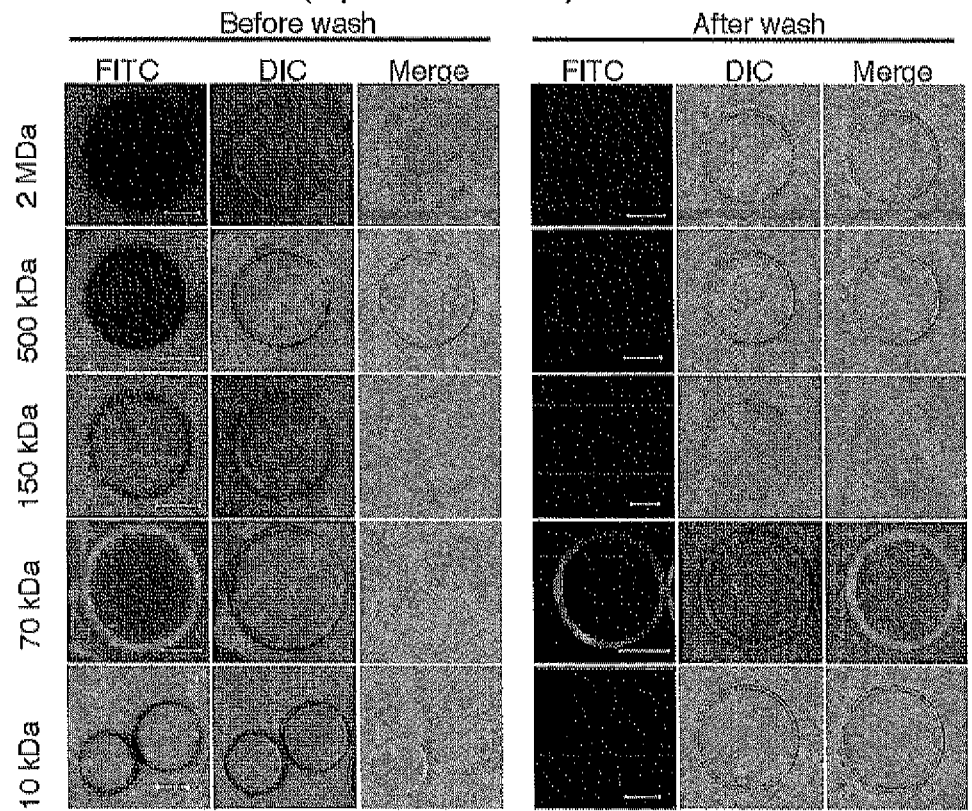
FIG. 3. Size exclusion limit determined using fluorescent dextrans.
Figure 3:
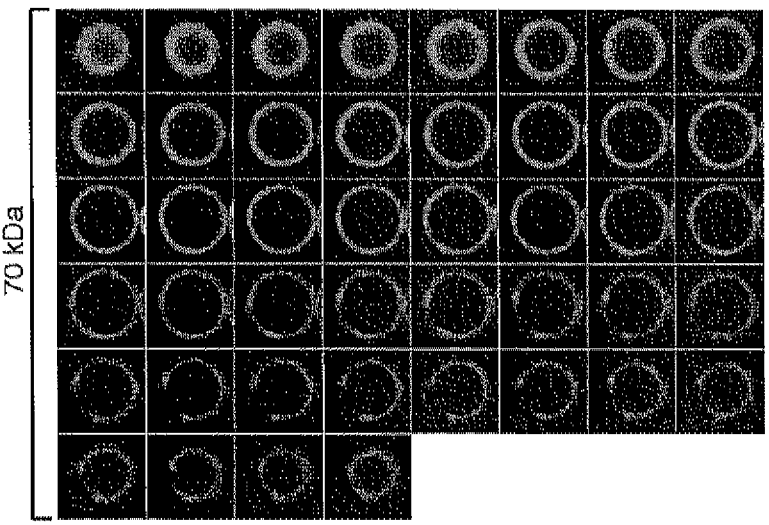
Figure 4:
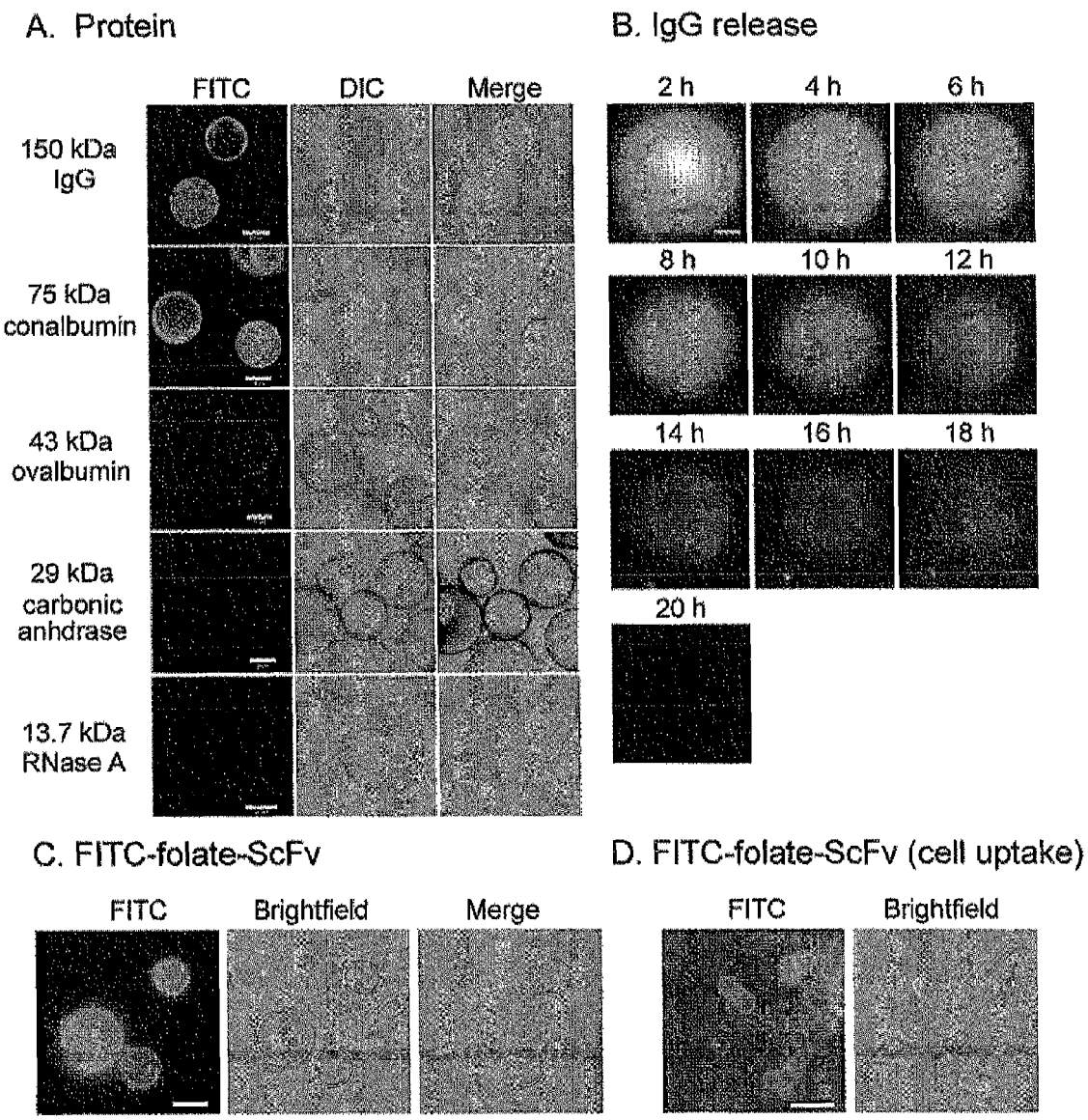
FIG. 4. Interaction of PW-HGMs with proteins.

Determination of size exclusion limit. To determine the empirical size exclusion limit for hydrated molecules, PW-HGMs were incubated with fluorescein-labeled cross-linked carbohydrate polymers (dextrans) of known size distribution. The average molecular weight and Stokes radius of each type of dextran are listed in Table 1. Confocal microscopy was used to monitor the presence of fluorescent dextran in the external space, interior cavity, and walls. Before washing to remove unbound dextran, the 150 kDa, 70 kDa, and 10 kDa dextrans were seen to equilibrate between the external space and interior volume (FIG. 3A). By contrast, the brightness of the 500 kDa dextran fluorescence was greater in the external space than in the interior, and the 2 MDa dextran was excluded from the interior. The results are consistent with an interpretation that the porous walls behave as molecular sieves, with the larger dextrans showing progressively less ability to enter the PW-HGM shell or cavity. Relatively little dextran fluorescence was detected within the porous walls, with the striking exception of the 70 kDa dextran, which accumulated to levels exceeding its concentration in solution (FIG. 3A, "After wash"). To illustrate that the 70 kDa dextran is indeed concentrated in the microsphere walls, a series of images is presented representing optical sections along the z-axis of PW-HGMs following washing (FIG. 3).

zation agent (Li et al., 2003, *Nucleic Acids Res;* 31:5848-57) was then tested. This scFv consists of the heavy- and light-chain variable portions of an IgG, joined by a flexible linker and expressed as a MBP fusion in *Escherichia coli*. The presence of MBP promotes stability in the intracellular environment (Shaki-Loewenstein et al., 2005, *J Immunol Methods;* 303:19-39) and results in a total molecular weight of 75 kDa, within the range that is retained by PW-HGMs (FIG. 4). The scFv was tagged with FITC to allow visualization and with folic acid to promote binding to high-affinity cell surface folate receptor alpha (Frα) (Zhao et al., 2008, *Expert Opin Drug Deliv;* 5:309-19). Like the similarly sized conalbumin, the FITCfolate-scFv derivative was taken up and retained by the PWHGMs (FIG. 4). The washed PW-HGMs were incubated with FRα-positive KB cells, and transfer of fluorescent protein to the cell surface receptors was evident (FIG. 4D).

TABLE 1

Interaction of dextrans, nucleic acids, and proteins with porous-wall hollow glass microspheres

| Material | | Mass | | Dimensions | Charge | Enter interior | Bind walls |
|---|---|---|---|---|---|---|---|
| Dextran | | 2 | MDa | 28.0 nm | Neutral | No | – |
| | | 500 | kDa | 14.4 nm | Neutral | No | – |
| | | 150 | kDa | 8.5 nm | Neutral | Yes | – |
| | | 70 | kDa | 6.0 nm | Neutral | Yes | +++ |
| | | 10 | kDa | 2.3 nm | Neutral | Yes | + |
| DNA | 55-nt duplex | 36.3 | kDa | 2.2 × 18 nm | Acidic | Yes | ++ |
| RNA | 21-nt duplex | 13.9 | kDa | 2.6 × 4.8 nm | Acidic | Yes | + |
| Protein | IgG | 150 | kDa | 5.3 nm | Varies, pI 5.0-7.5 | Yes | +++ |
| | Conalbumin | 75 | kDa | NA | Acidic, pI 5.9 | Yes | +++ |
| | Ovalbumin | 43 | kDa | 2.7 nm | Acidic, pI 4.6 | Yes | + |
| | Carbonic anhydrase | 29 | kDa | NA | Acidic, pI 6.6 | Yes | – |
| | Rnase A | 13.7 | kDa | 1.6 nm | Basic, pI 8.9 | Yes | – |
| | MBP-scFv | 75 | kDa | NA | Neutral, pI 6.8 | Yes | +++ |

MBP, maltose-binding protein; scFv, single-chain antibody variable fragment; NA, not available; nt, nucleotide(s).
Dimensions of dextrans are from Dong et al.,[33] and those for proteins are from Fasman.[34]
Dimensions of RNA and DNA are based on A-helix and B-helix parameters, respectively.[35]
Estimates of size and charge do not take into account fluorophore conjugation. Binding to walls was estimated visually.

Interaction of PW-HGMs with proteins was tested. The size-dependent interaction of PW-HGMs with macromolecules will be useful as controlled-release delivery vehicle for proteins. A set of test proteins was prepared by reacting well-characterized globular protein molecular-weight markers with FITC. The fluorescently labeled products were incubated with PW-HGMs, and the preparations were imaged by confocal microscopy before and after washing. All six of the tested proteins entered the interior volume initially. The two largest proteins, immunoglobulin G (IgG) and conalbumin, were retained following washing (FIG. 4A). The results were reminiscent of the 70 kDa dextran, with some protein apparently concentrated within the walls. To characterize the PW-HGM-protein interaction further, the rate of loss was measured during an extended observation period. Images of single PW-HGMs were collected at 2 hour intervals using a Deltavision microscope with point-visiting capability. The signal slowly disappeared with time (FIG. 4). Quantitative analysis of the fluorescence density showed that protein was lost with first-order kinetics for at least the first 10 hours, with a half-life of 6-7 hours. The image shown is representative of the median behavior in the population; some PW-HGMs had longer retention half-lives, whereas others lost fluorescence immediately upon washing, perhaps reflecting the presence of unseen defects in the wall structure.

The interaction of PW-HGMs with a therapeutic antibody fragment that is under development as a tumor radiosensiti- KB cells are derived from a human carcinoma and are commonly used in assays for the identification of anti-neoplastic agents and the effectiveness of anti-neoplastic therapies. Together, the results suggest that PW-HGMs may be useful for in vivo delivery of therapeutic antibodies and recombinant antibody derivatives.

Interaction of porous-wall hollow glass microspheres with nucleic acids. To further assess the controlled-release properties of the PWHGMs, their interactions with nucleic acids was explored. PW-HGMs were incubated with an annealed 55-mer DNA, which behaved much like the smaller dextrans, freely entering and exiting the interior volume, with some retention within the porous walls after washing (FIG. 5A). Then an siRNA composed of a pair of annealed 21 nucleotide RNAs was tested. SiRNAs are in widespread development as therapeutic agents, although efficient delivery methods are the limiting factor in many applications (Kim and Rossi, 2008, Biotechniques; 44:613-6; and Juliano et al., 2008, *Nucleic Acids Res;* 36:4158-71; Kim and Rossi, 2008, Biotechniques; 44:613-6; and Juliano et al., 2008, *Nucleic Acids Res;* 36:4158-71). Like the DNA oligonucleotide, siRNA freely equilibrated between the exterior medium and the interior cavity (FIG. 5B).

Figure 5:
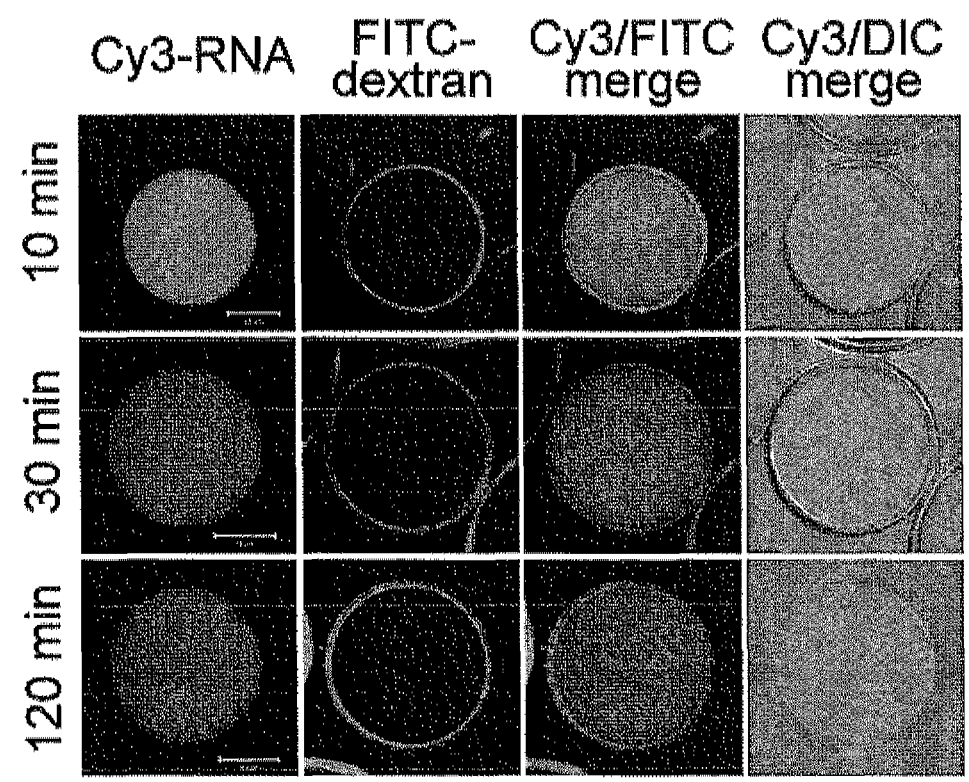
FIG. 5. Interaction of PW-HGMs with DNA and RNA oligonucleotides.

Based on the idea that the 70 kDa dextran was about the same size as the minimum diameter of the pores, it was next investigated whether it could be used to "gate" them so as to control the uptake or release of nucleic acid cargo. The PW-HGMs were loaded with Cy3-labeled siRNA, then incubated with fluorescein-labeled 70 kDa dextran. Before washing the RNA was seen inside the PW-HGMs, and the dextran was enriched within the walls (FIG. 5). After washing, some PW-HGMs retained the siRNA (although it leached out of others) (FIG. 5C). Time-lapse studies of release of siRNA from individual PW-HGMs were performed (FIG. 5D). The signal density for siRNA was bright initially and declined with time. This result supports the use of PW-HGMs as a controlled release delivery vehicle for siRNA.

Visualization of 70 kDa dextran-loaded PW-HGMs following intratumoral injection. The PW-HGMs are considerably larger than blood cells and are thus too large for systemic administration by an intravenous route. However, they are approximately the same diameter as the solid glass microspheres that have been used for tumor radioembolization. As a first step toward determining whether PW-HGMs could be used in a similar way, the fate of intratumorally injected 70 kDa dextran loaded microspheres in a mouse tumor model was examined. The sensitivity and linearity of the imaging system was first determined by loading PW-HGMs with FITC-labeled 70 kDa dextran, transferring them into the wells of an agarose gel, and imaging them. Quantitative image analysis revealed a linear relationship between the amount of material loaded and the corresponding photon counts (FIG. 6A). Then, 250 µL of the same PW-HGMs were injected intratumorally into a xenografted mouse. The anesthetized live mouse was imaged using the charge-coupled device camera system (Caliper Life Sciences, Hopkinton, Mass.). The image shows clear localization at the site of injection (FIG. 6B). The results suggest that PW-HGMs are retained at the site of intratumoral injection and thus could be used for localized delivery of antitumor antibodies or siRNA.

Discussion

This example presents an initial characterization of PW-HGMs, a unique material distinguished by large, solvent-accessible interior volume and mesoporous walls. Molecular dimensions seem to be the most important factor in determining the type of interactions between macromolecules and PW-HGMs. The porous walls function as molecular sieves, admitting dextrans with a Stokes radius up to 8.5 nm, whereas dextrans with a larger radius were progressively excluded. The walls also admitted up to at least 5.5 nm, as well as short double-stranded RNA and DNA molecules, which have a helical diameter of 2-3 nm. Results are consistent with prior measurements indicating ink bottle-shaped pores with a minimum, or limiting, diameter of ~10 nm.

Although oligonucleotides and small proteins freely equilibrated between the inside and the outside of the PW-HGMs, larger proteins in the 70 to 150 kDa range behaved differently, being retained after washing and slowly released on a time scale of several hours. The FITC-labeled 70 kDa dextran also had an anomalously strong affinity for the interior of the mesoporous walls, whereas the smaller and larger dextrans did not. Binding to the walls is likely greatest when the particle size distribution and the pore size distribution of the PW-HGMs have maximum overlap, because this allows a large fraction of the surface area of the particles to be in contact with the wall material at any given time, thus maximizing the opportunity for surface interactions. Assuming that there is a range of particle sizes and pore sizes, maximum overlap should occur somewhat below the absolute size exclusion limit. The data suggest that this might indeed be the case (i.e., the 150-kDa dextran equilibrated between the exterior and the interior, presumably by passing through a subset of pores at the larger end of the size distribution, but did not noticeably concentrate within the walls).

Based on its empirically determined affinity for the walls, the ability of the 70 kDa dextran to modulate the release of a small duplex RNA was tested. The dextran-gated PW-HGMs retained the oligonucleotide over a period of minutes to hours, whereas untreated PW-HGMs showed no long-term retention. This demonstrated ability to use one macromolecule to gate the release of another extends the possible range of applications of PW-HGMs as nanocarriers in biomedical applications. The initial characterization of PW-HGMs reported here used model proteins and nucleic acids that are well characterized and, in most cases, commercially available as fluorescent conjugates.

Example 1 has published as Li et al., ("Porous-wall hollow glass microspheres as novel potential nanocarriers for biomedical applications") *Nanomedicine* 20101 February 6; 6(1):127-136 Epub 2009 Jul. 16.

Example 2

Administration of an siRNA

Following procedures described in more detail in Example 1, compositions of porous-wall hollow glass microspheres containing an siRNA within the internal volume of the microspheres will be injected into a tumor. Such compositions may also be administered intravascularly to embolize a tumor. The tumor may be a liver or brain cancer. The composition may also include a gating agent, such as dextran 20, dextran 40, dextran 60, dextran 70, colloidal starch, or polyvinylpyrrolidone.

Example 3

Administration of an scFv

Following procedures described in more detail in Example 1, compositions of porous-wall hollow glass microspheres containing an scFv within the internal volume of the microspheres will be injected into a tumor. Such compositions may also be administered intravascularly to embolize a tumor. The tumor may be a liver or brain cancer. The ScFv may be scFv 18-2. After delivery of the scFv/microsphere composition, the tumor may be exposed to radiation. The composition may also include a gating agent, such as dextran 20, dextran 40, dextran 60, dextran 70, colloidal starch, or polyvinylpyrrolidone.

The complete disclosure of all patents, patent applications, and publications, and electronically available material (including, for instance, nucleotide sequence submissions in, e.g., GenBank and RefSeq, and amino acid sequence submissions in, e.g., SwissProt, PIR, PRF, PDB, and translations from annotated coding regions in GenBank and RefSeq) cited herein are incorporated by reference. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

All headings are for the convenience of the reader and should not be used to limit the meaning of the text that follows the heading, unless so specified.

What is claimed is:

1. A hollow microsphere comprising:

a glass wall surrounding an internal volume to form a glass microsphere having a diameter of about 10 microns to about 100 microns, wherein the glass wall comprises an external surface and an internal surface, and dextran-gated channels having a diameter of about 1 nm to about 100 nm connecting the external surface and the internal volume, wherein the internal volume comprises a biopolymer and wherein the dextran-gated channels passively regulate passage of the biopolymer out of the hollow microsphere.

2. The hollow microsphere of claim 1, wherein the hollow microsphere has a diameter ranging from about 20 microns to about 50 microns.

3. The hollow microsphere of claim 1, wherein the channels have a diameter of about 10 nanometers (nm).

4. The hollow microsphere of claim 1, wherein the biopolymer is selected from the group consisting of an antibody or antigen-binding fragment or derivative thereof, a protein, a nucleic acid, a hormone, a growth factor, a virus, and combinations thereof.

5. The hollow microsphere of claim 1, wherein the biopolymer comprises a single chain Fv.

6. The hollow microsphere of claim 1, wherein the biopolymer comprises a short interfering RNA (siRNA) or an antisense RNA.

7. The hollow microsphere of claim 1, wherein the biopolymer has a size of about 3 nanometers to about 8 nanometers.

8. The hollow microsphere of claim 1, wherein the channels have a diameter of a size of about the same size of the biopolymer.

9. The hollow microsphere of claim 1, wherein the channels have a diameter of a size greater than the size of the biopolymer.

10. The hollow microsphere of claim 1, wherein the gated channels comprise a gating agent having a diameter about the same as the of the channels.

11. The hollow microsphere of claim 10, wherein the gating agent promotes retention of the biopolymer within the internal volume of the hollow microsphere.

12. A composition comprising the hollow microsphere of claim 1.

13. A method of providing a biopolymer to a subject, the method comprising administering a composition comprising the hollow microsphere of claim 1 to the subject.

14. The method of claim 13 wherein the composition is administered intratumorally.

15. The method of claim 13 wherein the composition is administered via the hepatic artery.

* * * * *